United States Patent [19]

Terao et al.

[11] 4,199,531

[45] Apr. 22, 1980

[54] INTERMEDIATES FOR THE PRODUCTION OF QUINONES

[75] Inventors: Shinji Terao, Toyonaka; Kaneyoshi Kato, Suita, both of Japan

[73] Assignee: Takeda Chemical Industries, Ltd., Osaka, Japan

[21] Appl. No.: 840,806

[22] Filed: Oct. 11, 1977

[30] Foreign Application Priority Data

Oct. 19, 1976 [JP] Japan .............................. 51/125736
Jul. 20, 1977 [JP] Japan .............................. 52/87674
Jul. 20, 1977 [JP] Japan .............................. 52/87675

[51] Int. Cl.$^2$ ................ C07C 147/06; C07C 147/14; C07C 43/22
[52] U.S. Cl. ................ 260/607 AR; 260/345.9 R; 260/347.2; 260/347.8; 260/347.91; 260/396 R; 260/396 K; 260/609 F; 568/633; 568/645; 568/649; 568/652; 568/654; 568/734; 568/736
[58] Field of Search ........ 260/607 AR, 609 F, 613 D, 260/613 R; 568/645, 649

[56] References Cited

U.S. PATENT DOCUMENTS

| | | | |
|---|---|---|---|
| 3,068,295 | 12/1962 | Folkers et al. ................... | 260/613 D |
| 3,781,313 | 12/1973 | Julia .............................. | 260/607 AR |
| 3,960,967 | 6/1976 | Olson et al. ................... | 260/607 AR |
| 4,038,323 | 7/1977 | Chabardes ..................... | 260/607 AR |
| 4,089,873 | 5/1978 | Rapoport et al. ............... | 260/613 D |

FOREIGN PATENT DOCUMENTS 49-42627  4/1974  Japan ..................................... 260/609 F
1396622  6/1975  United Kingdom .

OTHER PUBLICATIONS

Y. Masaki et al., Abstr. Rep. (97th Pharm. Soc. Japan), II, 167 (1977), "Addition of Benzenesulfenyl Chloride to Geranyl and Neryl Derivatives and its Application".
P. Grieco et al., J. Org. Chem., 39, 2135 (1974), "A General 1,5-Diene Synthesis, Application to the Synthesis of Squalene".
L. Altman et al., Synthesis, 129 (1974), "A New, Highly Stereoselective Synthesis of all trans-Geranylgeraniol".
R. Ruegg et al., Helv. Chim. Acta, 42, 2616 (1959), "Synthesis of Ubiquinone (45) and Ubiquinone (50)".
S. Inoue et al., Bull. Chem. Soc. Japan, 47 (12), 3098 (1974), "The Synthesis of Coenzyme Q".
C. Shunk et al., J. Amer. Chem. Soc., 81, 5000 (1959), "Coenzyme Q. X. Synthesis of Coenzyme $Q_9$ . . . and a Vitamin K Analog".

*Primary Examiner*—Alton D. Rollins
*Assistant Examiner*—M. C. Eakin
*Attorney, Agent, or Firm*—Hubbell, Cohen, Stiefel & Gross

[57] ABSTRACT

A novel method for producing hydroquinone and quinone derivatives by a regio- and stereo-specific coupling reaction of hydroquinone derivative having a terminal activated (poly)prenyl side chain with a prenyl derivative. This method can provide in good yield various hydroquinone and quinone derivatives having any prenyl length of the side chain.

14 Claims, No Drawings

INTERMEDIATES FOR THE PRODUCTION OF QUINONES

This invention relates to a novel method for the production of quinones.

It is an object of this invention to provide a process for the regio-selective chemical modification of the double bond of the terminal prenyl group in a quinone compound with a polyprenyl side chain and further succeeded in the introduction of a reactive functional group into the trans methyl group of said terminal prenyl group. It is a further object of this invention to provide a commercially advantageous method for the production of known important biologically active quinones or their intermediates through the stereo-selective transformation and coupling reaction of a protected quinol having a (poly)prenyl side chain which is activated at the terminal prenyl group with an appropriate polyprenyl component.

Description of the Invention

This invention is directed to:

(1) A method for producing a hydroquinone or quinone derivative of the formula

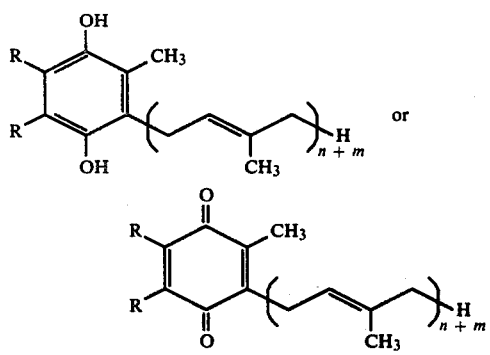

wherein each R is methyl or methoxy, or the two R-groups, taken together, represent a group of the formula —CH=CH—CH=CH— or —CH₂—CH= CH—CH₂—, n is an integer 1 to 9 inclusive and m is an integer 1 to 11 inclusive, the sum of n and m being an integer 2 to 12 inclusive, which comprises reacting a hydroquinone derivative of the formula

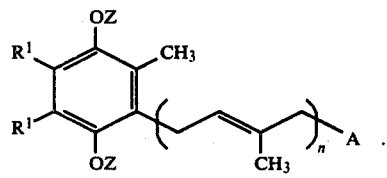

wherein each $R^1$ is methyl or methoxy, or the two $R^1$-groups, taken together, represent a group of the formula —CH=CH—CH=CH—, Z is a protective group, A is halogen, arylthio, arylsulfinyl or arylsulfonyl, and n has the same meaning defined above, with a prenyl derivative of the formula

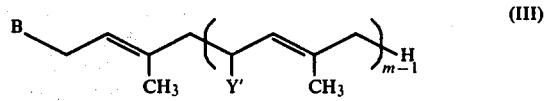

wherein B is halogen in a case where the above A is arylthio, arylsulfinyl or arylsulfonyl, or B is arylthio, arylsulfinyl or arylsulfonyl in a case where the above A is halogen; Y' is hydrogen, arylthio, arylsulfinyl or arylsulfonyl, and m has the same meaning defined above, and then subjecting the resulting coupled compound to reductive desulfurization and, if necessary, further to a reaction for the removal of the protective group and/or oxidation. (2) A method for producing the hydroquinone or quinone derivative (Ia) or (Ib), which comprises subjecting a compound of the formula

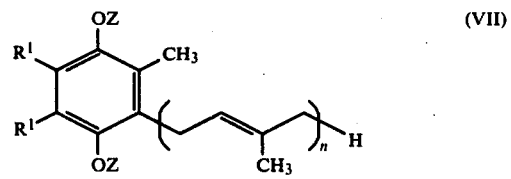

wherein $R^1$, Z and n have the meanings respectively defined above, or its quinone derivative, to epoxidation at its terminal prenyl group to obtain an epoxy derivative of the formula

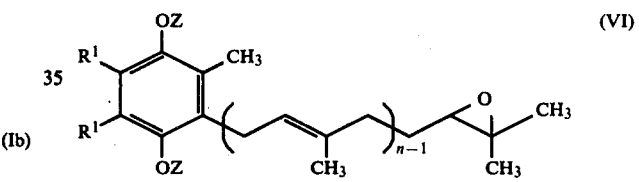

wherein $R^1$, Z and n have the meanings respectively defined above, or its quinone derivative, subjecting the epoxy derivative or its quinone derivative to an epoxy-cleavage reaction to obtain an allyl alcohol derivative of the formula

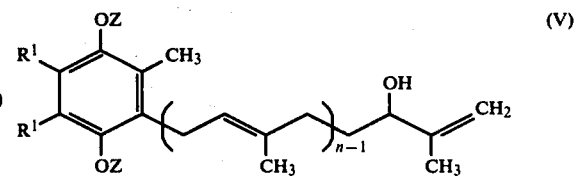

wherein $R^1$, Z and n are as previously defined or its quinone derivative, the last-mentioned quinone derivative is then subjected to reduction and a reaction for introduction of protective groups to give the hydroquinone type allyl alcohol derivative (V), halogenating the allyl alcohol derivative (V) and, if necessary, then reacting the resulting halogenohydroquinone derivative with an alkali arylthiolate or an alkali arylsulfinate, and further, if necessary, subjecting the resulting compound, when it is the arylthio derivative, to oxidation, to obtain the hydroquinone derivative (IV), reacting said hydroquinone derivative (IV) with the prenyl derivative (III), and then subjecting the resulting coupled compound to reductive desulfurization and, if necessary, to a reaction for the removal of the protective group and/or to oxidation.

Referring to each of the above formulas, the protective group Z may be any of the groups commonly employed capable of protecting a hydroxyl group. Thus, methyl, lower alkoxymethyl such as methoxymethyl and ethoxymethyl, benzyl, tetrahydropyranyl, tetrahydrofuranyl, etc. may be mentioned with methyl, methoxymethyl, ethoxymethyl and benzyl being preferred examples. Among them, benzyl and ethoxymethyl are most preferred.

The halogen designated by A and B may for example be chlorine, bromine or iodine, with chlorine and bromine preferred. The aryl moiety of the arylthio, arylsulfinyl or arylsulfonyl group designated by A, B and Y' may be for example phenyl, naphthyl, p-methylphenyl (tolyl), p-methoxyphenyl or benzyl, with phenyl and p-methylphenyl preferred. The aryl moiety of arylsulfonyl, particularly p-toluenesulfonyl and phenylthio are preferred employed.

The compound (VII) or its quinone derivative, i.e.

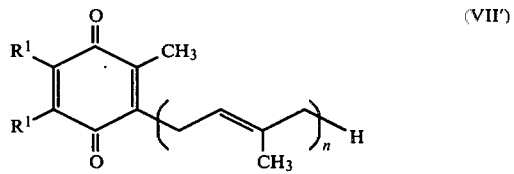

[wherein $R^1$ and n have the meanings respectively defined above]

(Hereinafter, "quinone derivative" means "derivative

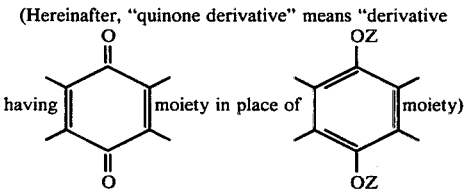

employed as a starting material in the method of this invention is one of the known hydroquinone or quinone derivative or a derivative prepared in a manner analogous to the production of such known derivatives. For example, in order to produce ubiquinone-8, ubiquinone-9 or ubiquinone-10 as the final product, the known ubiquinone-n (where n is an integer from 1 to 9) or the corresponding hydroquinone is employed as the starting material. For the production of menaquinone-4 or menaquinone-5, for instance, as the final product, 2-methyl-3-prenyl-1,4-dimethoxynaphthalene, 2-methyl-3-polyprenyl-1,4-dimethoxynaphthalene or the like is employed as the starting material. When it is desired to produce a material for the synthesis of α-tocotrienol, for instance, 1,4-dimethoxy-2,3,5-trimethyl-6-prenylbenzene, 1,4-dimethoxy-2,3,5-trimethyl-6-polyprenylbenzene or the like is employed.

The starting compound (VII) or (VII') is subjected to the epoxidation of its terminal prenyl group to obtain the corresponding epoxy derivative (VI) or its quinone derivative (VI'). This reaction features regio-specific modification of the terminal group of the side chain of the starting compound and, for this purpose, it is advantageous to first conduct a halohydrination reaction to produce a halohydrin compound of the formula (VIII) or (VIII') given below and then epoxidize this halohydrin compound. The halohydrination reaction may for example by bromohydrination or chlorohydrination, the former reaction being particularly desirable. In this epoxidation reaction via such a halohydrin compound, especially via a bromohydrin compound, a regio-specificity is effected. Namely, the epoxy ring can be formed selectively only at the terminal double bond. This regio-specific effect is attained especially in cases where n in starting compound (VII) or (VII') is not less than 3.

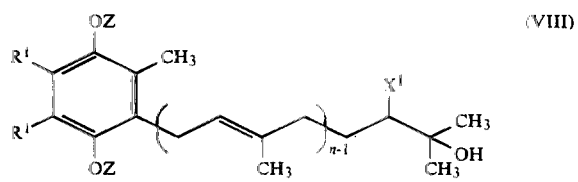

or its quinone derivative (VIII') [wherein $R^1$, Z and n have the meanings respectively defined hereinbefore; $X^1$ is halogen]

The halogen atom $X^1$ may for example be bromine or chlorine.

The above halohydrination reaction is accomplished by reacting the starting compound (VII) or (VII') with an active halogen derivative. This reaction is preferably conducted normally in an aqueous organic solvent at a temperature between about $-10°$ C. and about $10°$ C. Examples of such active halogen derivative are hypochloric acid, hypobromic acid, hypochlorites (e.g. sodium salt, potassium salt), hypobromites (e.g. sodium salt, potassium salt), N-chlorosuccinimide, N-bromosuccinimide (NBS), N-chloroacetamide, N-bromoacetamide; N-chlorophthalimide, N-bromophthalimide, etc. The ratio of such active halogen derivative to the starting compound is preferably from about one to two times stoichiometric amounts. The aforesaid aqueous organic solvent may be any organic solvent that does not interfere with the reaction. Preferably it is a water-miscible organic solvent such as tetrahydrofuran, tert-butanol, 1,2-dimethoxyethane, acetic acid, dimethylsulfoxide, dimethylacetamide or dimethylformamide. The water content of such an aqueous organic solvent depends somewhat upon the solubility of the halohydrin compound (VIII) or (VIII') in the solvent employed in the halohydrination step. The water content normally ranges from about 5 to about 30 volume % and, preferably, about 10 to 20 volume %. This reaction proceeds quickly and normally goes to completion within about 1 to 10 hours.

The halohydrin compound (VIII) and (VIII') thus produced as separated from the reaction mixture by a routine separation-purification procedure and, then is, subjected to the next reaction. Alternatively, the very reaction mixture may be used in the next reaction.

By treating this halohydrin compound (VIII) or (VIII') with a base, there can be obtained the epoxy derivative (VI) or its quinone derivative (VI'). The base just mentioned may desirably be sodium hydroxide, potassium hydroxide, sodium carbonate or potassium carbonate. The amount of the base is preferably about once to twice as much as the equimolar amount. The reaction is normally conducted in an organic solvent or an aqueous organic solvent. Among preferred organic solvents are methanol, ethanol, tetrahydrofuran, tert.-butanol, 1,2-dimethoxyethane, dimethylsulfoxide, dimethylacetamide, dimethylformamide, etc. These solvents may be used as they are or in admixture with water. The water content is normally within the range of about 10 to 20 volume %. The reaction is normally conducted at room temperature, although it may be carried out at an elevated temperature, if necessary.

As to the epoxidation reaction mentioned above, where n in starting material (VII) or (VII') is 2 or less, an epoxy derivative (VI) or (VI') can be obtained also by reacting the starting material with a per-acid in a manner known per se in a single step. The per-acid may for example be peracetic acid, performic acid, monoperphthalic acid or m-chloroperbenzoic acid.

The epoxy derivative (VI) or (VI') may be isolated from the reaction mixture by a routine separation-purification procedure.

Alternatively, it may be subjected to the next epoxy-cleavage reaction step without purification. By this epoxy-cleavage reaction, said derivative is converted to an allylalcohol derivative (V) or its quinone derivative (V').

This reaction may be accomplished by whichever of the following two procedures.

In a first of the procedures, the epoxy derivative (VI) or (VI') is either hydrolyzed in the presence of an acid catalyst or heated with sodium acetate or potassium acetate in glacial acetic acid to prepare a diol derivative of the following formula:

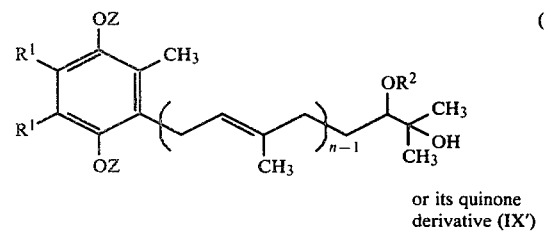

or its quinone derivative (IX')

[wherein $R^1$, Z and n are as previously defined; $R^2$ is hydrogen or acetyl]

The above diol derivative, in which $R^2$ is hydrogen, can be obtained by hydrolysis of epoxy derivative (VI) or (VI') in the presence of an acid catalyst. The acid catalyst is preferably sulfuric acid or perchloric acid, for instance. The hydrolysis reaction is normally carried out in an aqueous organic solvent which may be one of those mentioned for the halohydrination reaction. The compound in which $R^2$ is acetyl may be obtained by heating (VI) or (VI') with sodium acetate or potassium acetate in glacial acetic acid. The heating temperature is preferably about 50° C. to 70° C. The amount of sodium or potassium acetate is preferably about 4 to 10 times its stoichiometric amount. The diol derivative wherein $R^2$ is hydrogen is first acetylated in a manner known per se (e.g. in acetic anhydride-pyridine) to the diol in which $R^2$ is acetyl before using it in the next reaction.

As the diol derivative (IX) or (IX') in which $R^2$ is acetyl is treated with a dehydrating agent, there is obtained an allyl acetate derivative of the following formula.

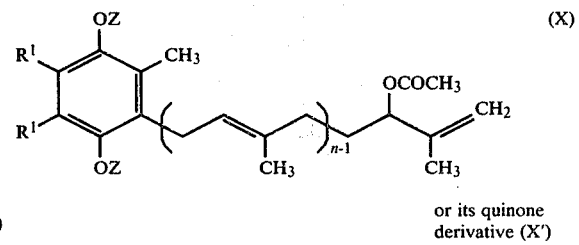

or its quinone derivative (X')

[wherein $R^1$, Z and n are as previously defined].

Among preferred reagents for said dehydration are thionyl chloride, phosphorus oxychloride, etc. This dehydration reaction is normally carried out in a non-polar solvent and in the presence of an organic base. As examples of said non-polar solvent may be mentioned n-hexane, cyclohexane, tetrahydrofuran, methylene chloride, chloroform, etc. The organic base may for example by pyridine or triethylamine. Usually this reaction is conducted under cooling, preferably at a temperature between about −20° C. and 20° C.

The resulting allyl acetate derivative (X) or (X') can be hydrolyzed under alkaline conditions to an allyl alcohol derivative (V) or its quinone derivative (V'). This reaction readily proceeds in an aqueous organic solvent and in the presence of a base (e.g. sodium hydroxide or potassium hydroxide. The aqueous organic solvent may be any of such solvents mentioned for the halohydrination reaction. Since the quinoid structure is unstable under alkaline hydrolysis conditions, it is preferable to conduct the hydrolysis under nitrogen gas in the presence of a reducing agent (e.g. sodium hydrosulfite or sodium borohydride) in aqueous methanol or aqueous ethanol.

The second procedure for accomplishing the epoxy-cleavage reaction comprises treating the epoxy derivative (VI) with a lithium dialkylamide to obtain an allyl alcohol derivative (V) in a single step. Normally this reaction is preferably conducted in an anhydrous solvent (e.g. absolute ether, dry tetrahydrofuran) using about 2 to 6 equivalents of a lithium dialkylamide, under an inert gas at about −10° C. to about 50° C. As preferred reagent for this reaction. There may be used lithium diethylamide, lithium diisopropylamide or lithium dicyclohexylamide.

The allyl alcohol derivative (V) or (V') thus produced can be isolated from the reaction mixture by a routine separation-purification procedure.

Where said derivative is a quinone compound (V'), it is first converted to the hydroquinone compound (V) by reduction, followed by protection of the hydroxy groups of the hydroquinone and, then, subjected to the next step, i.e., halogenation. Sodium hydrosulfite and sodium borohydride may be used as such preferred reducing agents. As preferred reactions for introducing protective groups, benzylation, methylation and methoxymethylation may be mentioned by way of example.

The halogenation of allyl alcohol derivative (V) yields the hydroquinone derivative (IV) wherein A is halogen. This halogenation is conducted by reacting (V) with a halogenating agent in an organic solvent. Preferred organic solvents for this purpose are such non-polar solvents as n-hexane, cyclohexane, tetrahydrofuran, methylene chloride and chloroform. Usually the halogenating agent is preferably a chlorinating agent or brominating agent, as exemplified by thionyl chloride, phosphorus oxychloride, thionyl bromide, phosphorus tribromide, etc. The amount of such halogenating agent is preferably about once to twice its stoichiometric amount. The reaction is normally conducted at room temperature or under ice-cooling. The resulting hydroquinone derivative (IV) wherein A is halogen can be isolated by a routine separation-purification procedure.

In a case where the hydroquinone derivative of (IV) wherein A is arylthio or arylsulfonyl is desired, the halogenohydroquinone derivative obtained above is further reacted with an alkali arylthiolate or an alkali arylsulfinate. The reaction is conducted in a suitable solvent such as dimethylformamide, dimethylacetamide, or dimethylsulfoxide at a temperature from −10° to 50° C. For example, sodium phenylthiolate and sodium p-toluene thiolate, and sodium phenylsulfinate and sodium p-toluene sulfinate are preferable as alkali arylthiolate and alkali arylsulfinate, respectively.

The hydroquinone derivative (IV) wherein A is arylsulfinyl can be obtained by oxidizing the compound (IV) wherein A is arylthio. The oxidation of arythio compound (IV) with hydrogen peroxide is effected in the presence of a heavy metal ion such as tungstic acid or molybdic acid.

The hydroquinone derivative (IV) thus produced is reacted with a prenyl derivative (III) to give a coupled compound, which in turn, is subjected to a reductive 1,2-dimethoxyethane or hexamethyl phosphoramide. This reaction is preferably carried out as follows:

First, the base is added to one of the compound (III) or (IV) wherein B or A is arylthio, arylsulfinyl or arylsulfonyl group in the above solvent under inert gas atmosphere (e.g. nitrogen, helium or argon) to produce the carbanion of said compound, and then, the other compound (IV) or (III) wherein A or B is halogen is gradually added to the mixture.

An amount of the base is normally from one to two times the stoichiometric amount. In a case where the prenyl derivative (III) contains two or more of arylthio, arylsulfinyl or arylsulfonyl group, it is desirable to employ about 0.8 to 1.2 times molar amounts of the base to the number of these groups. While the molar ratio of (III) and (IV) depends upon their properties of the particular compound (III) and (IV) employed for the coupling reaction, it is normally allowed to use each coupling component in a ratio of about 1:1.

The coupling reaction is usually conducted at a temperature in the range of about −78° C. to about 20° C., and the temperature at which halogeno compound (IV) or (III) is added is preferably not higher than around 0° C. After the addition of the compound has been completed, the reaction temperature is gradually warmed to room temperature, whereby the reaction is completed.

In this coupling reaction, one of the following three types of the coupled compounds may be produced by selecting the starting compounds (IV) and (III).

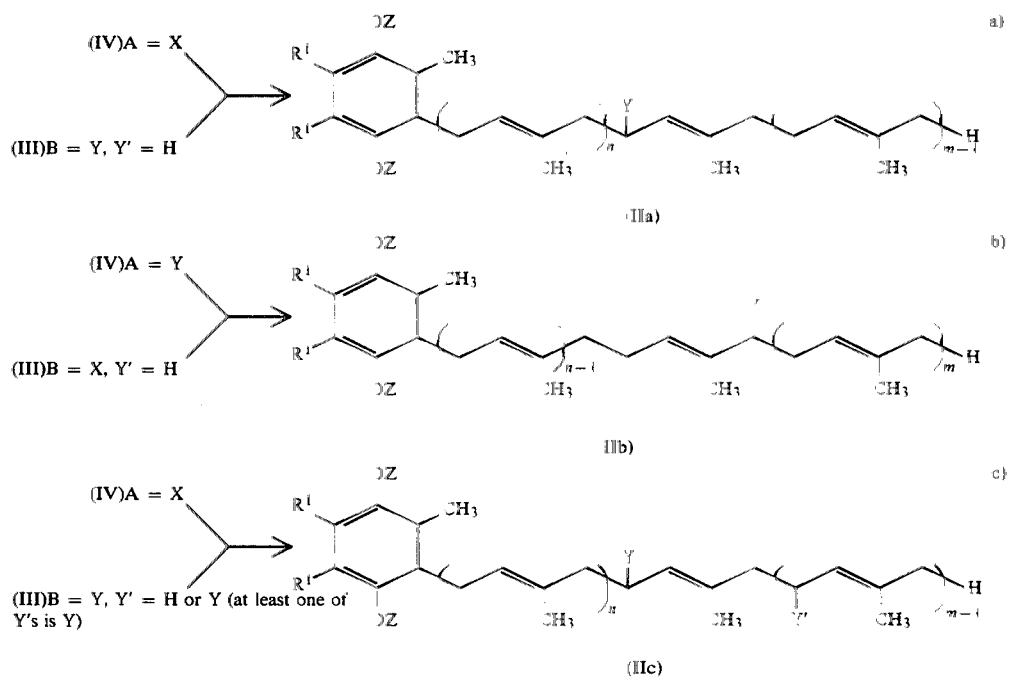

desulfurization and, if necessary, is further subjected to a reaction for removal of the protective groups and/or oxidation, to obtain the contemplated hydroquinone derivative (Ia) or quinone derivative (Ib).

The above compling reaction of (IV) with (III) is preferably conducted under basic conditions. The base to be employed may for example be n-butyllithium or phenyllithium. The reaction is usually carried out in an anhydrous organic solvent. The preferred solvent for this purpose may for example be tetrahydrofuran, ether,

[wherein A, B, $R^1$, Z, Y', n and m have the same meanings as defined hereinbefore; X is halogen; Y is arylthio, arylsulfinyl or arylsulfonyl; H is hydrogen]

M is preferably an integer 1 to 9 inclusive in the above (a) and (b), and an integer 2 to 11 inclusive in the above (c).

The isolation of the coupled compound (IIa), (IIb) or (IIc) can be accomplished by a routine separation-purification procedure. If necessary, a small amount of acid (e.g. acetic acid, hydrochloric acid or phosphoric acid) may be added to the reaction mixture to neutralize the system before isolation of said coupled compound.

The resulting coupled compound (IIa), (IIb) or (IIc) is then subjected to reductive desulfurization to eliminate the group Y, i.e. arylthio, arylsulfinyl or arylsulfonyl group. This reductive desulfurization method may be any one so long as the elimination of Y is attained. For example, an alkali metal may be permitted to act upon the coupled compound in an amine solvent. The amine as a solvent for this purpose includes lower alkalamines such as $C_{1-3}$ alkylamines (e.g. ethylamine, diethylamine, methylamine, dimethylamine, etc.) and ammonia, for instance, with ethylamine and ammonia being particularly preferred. As examples of the alkali metal include lithium, sodium and potassium, with lithium being particularly preferred. The amount of alkali metal is about one to five times its stoichiometric amount. This reaction is preferably conducted in inert gas and the reaction temperature is desirably in the range of about $-50°$ C. to about $0°$ C.

This reductive desurfurization results in the following; where the two $R^1$ groups in compound (IIa), (IIb) or (IIc) are joined together to represent —CH=CH—CH=CH—, the removal of Y may be accompanied by a reduction of this —CH=CH—CH=CH— group to yield the contemplated compound wherein two R-groups are jointed together to represent a group —CH$_2$—CH=CH—CH$_2$—; and where the protective group Z on compound (II) is a group which is reductively removable (e.g. benzyl), this desurfurization may remove the protective group Z simultaneously with the removal of Y to yield the desired compound (Ia) directly. Where a quinone derivative (Ib) is desired as the end product, the hydroquinone derivative may be subjected to a known oxidation (e.g. oxidation with ferric chloride, air oxidation or oxidation with silver oxide), whereby it can be easily converted to the quinone derivative (Ib).

Where the protective group Z is a group which is not removed by the aforesaid reaction for the elimination of Y (e.g. where Z is methyl, methoxymethyl or ethoxymethyl), the desired compound (Ia) or (Ib) can be easily obtained by way of a known reaction for removing the particular protective group (e.g. oxidation, hydrolysis). By way of illustration, where the protective group Z is methyl, methoxymethyl, or ethoxymethyl, the desired compound (Ib) can be obtained by permitting silver oxide (AgO) to act upon the desurfurized compound under acidic conditions (e.g. in the presence of nitric acid). Where the protective group Z is methoxymethyl or ethoxymethyl, the contemplated compound (Ia) can be obtained also by hydrolysis in the presence of an acid catalyst (e.g. hydrochloric acid, sulfuric acid, perchloric acid).

The end product (Ia) or (Ib) can be isolated from the reaction mixture by a routine separation-purification procedure. It should be noted that, as aforesaid, the hydroquinone derivative (Ia) and quinone derivative (Ib) can be easily inter-converted by an oxidation or reduction reaction known per se.

The method of this invention is stereospecifically applicable to both geometrical isomers (cis-and trans-isomers) at the double bond in the prenyl moiety of each compound. Therefore, it is possible to ensure that all the prenyl units in the product will sterospecifically have the trans-orientation. It is also possible to selectively introduce one or more cis-prenyl units. Thus, the method of this invention encompases those isomers as well.

The method of this invention permits a profitable commercial-scale production of the known hydroquinone and quinone derivatives such as ubiquinone compounds (e.g. ubiquinone-8, ubiquinone-9, ubiquinone-10) and menaquinone derivatives (e.g. menaquinone-4, menaquinone-5) which are useful as medicines or intermediates for the production of medicines, and further α-tocoquinone derivatives (R=CH$_3$) prepared by this method are useful to obtain tocopherol type compounds having Vitamin E effect, especially tocoquinone-4 while can be converted to known tocopherol or tocotrienol by known procedure [Helv. Chim. Acta., 46, 2517 (1963)].

Thus, in the method of this invention, by a selective combination of n in starting compound (IV) or, (VII) or (VII') with m in prenyl derivative (III), a quinone compound (Ia) or (Ib) having a desired length of polyprenyl side chains can be regio- and stereo-specifically produced in a fewer number of steps and in improved yield. Thus, for example, ubiquinone-10 (Ib, R=CH$_3$O, n+m=10) can be produced in good yield from ubiquinone-1(VII', $R^1$=CH$_3$O, n=1) and solanesol derivative (III, m=9). Therefore, the method is commercially very advantageous and useful for production of quinones with a polyprenyl side chain, where the end product (Ia) or (Ib) is such that the two R-groups are joined together to form a group of the formula —CH$_2$—CH=CH—CH$_2$—, this particular compound (Ia) or (Ib) is a novel compound and this compound can be easily converted to the end product (Ia) or (Ib) in which said two R-groups represent —CH=CH—CH=CH— as taken together, by means of a known oxidation (e.g. oxidation with dichlorodicyano-1,4-benzoquinone).

The hydroquinone derivative (IV) employed in the present method can be produced also by the following reaction processes.

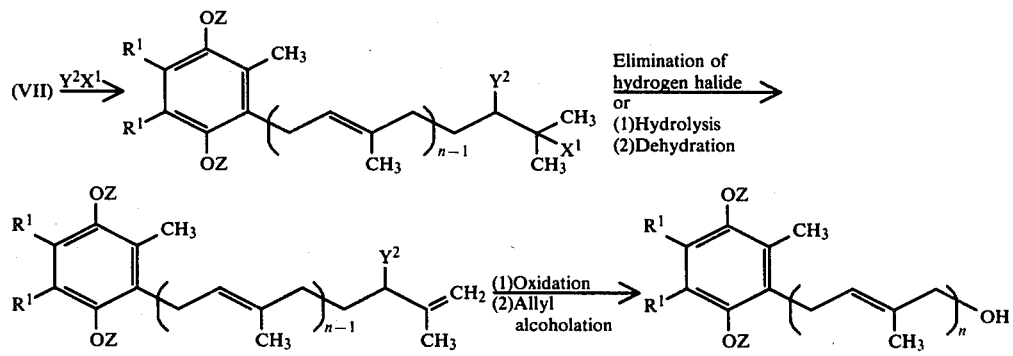

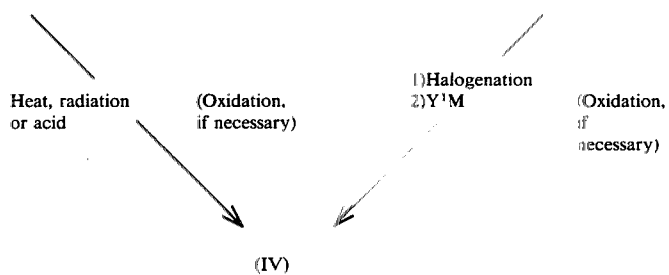

(IV)

[wherein $R^1$, Z and n are as previously defined; M is an alkali metal; $Y^1$ is arylthio or arylsulfonyl; $Y^2$ is arylthio; $X^1$ is halogen.]

The above reaction processes are shown for the production of hydroquinone derivatives by way of example but these reactions may be preceded by the conversion of such derivatives to the corresponding quinone derivatives.

While some of the starting compounds (III) are novel ones, these compounds can be easily prepared for example by the following processes. Namely, the prenyl derivative (III) wherein B is halogen can be produced by a method which comprises halogenating a compound of the formula

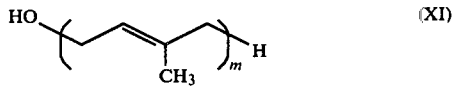

(XI)

wherein m has the meaning defined hereinbefore. The prenyl derivative (III) wherein B is arylthio or arylsulfonyl can be produced by reacting the resulting halogenoprenyl compound (III) with an alkali thiolate (e.g. sodium phenylthiolate, sodium benzylthiolate), an alkali sulfinate (e.g. sodium benzenesulfinate, sodium p-toluenesulfinate) or the like so as to introduce the arylthio or arylsulfonyl group. The prenyl derivative (III) wherein B is arylsulfinyl can be produced by oxidizing the arylthioprenyl derivative (III).

Further, the above compound (XI) having a desired number of m can be obtained by a process known per se for an elongation reaction of the prenyl chain.

The prenyl derivative (III) wherein at least one of Y's is arylthio, arylsulfinyl or arylsulfonyl can be produced by regio-specifically halogenating the terminal prenyl group of (III) wherein B is arylthio, arylsulfinyl or arylsulfonyl in accordance with a similar procedure to that of the present invention, and then reacting the resulting halogeno compound with the prenyl derivative (III) wherein B is arylthio, arylsulfinyl or arylsulfonyl in accordance with a similar coupling reaction to that of the present invention. Thus, these processes are illustrated by the following reaction scheme:

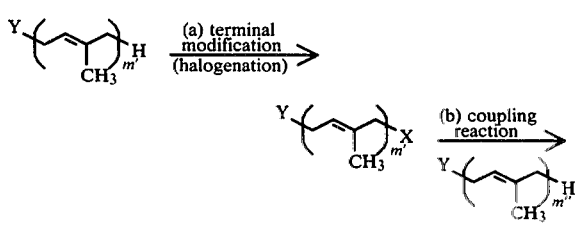

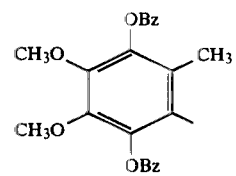

(III)
B = Y, Y' = H or Y
(at least one of Y's is Y)

[wherein Y, X, B, Y' and H have the meanings respectively defined hereinbefore; each m' and m" is an integer 1 to 9 inclusive.]

The starting compound (VII) can be easily produced by a process which comprises reducing a known quinone derivative (VII') in a manner known per se to the hydroquinone compound and subjecting the last-mentioned compound to a reaction for the introduction of protective groups (e.g. benzylation, methylation, methoxymethylation, etc).

The production intermediates in the method of this invention, i.e. compounds of the formulas (IIa), (IIb), (IIc), (IV), (V), (V'), (VI), (VI'), (VIII), (VIII'), (IX), (IX'), (X) and (X'), are all novel compounds which are novel intermediates very valuable for a commercially advantageous production of quinone compounds (Ia) and (Ib). Therefore, this invention additionally provides those novel intermediates and processes for their production.

The following examples are intended to further illustrate this invention and should by no means be construed as limiting the scope of the invention. It should also be understood that, as used in those examples, K represents a group of the formula

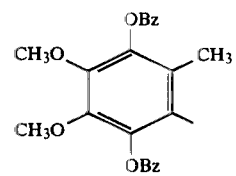

(Bs means benzyl); Ts represents p-toluenesulfonyl; and NMR spectra show in δ value in deuteriochloroform with TMS as the internal reference.

REFERENCE EXAMPLE 1

In dimethylformamide (20 ml) was dissolved 1-bromo-3-methyl-butene(1.49 g, 10 m moles) and sodium p-toluenesulfinate dihydrate (2.5 g, 1.16 equiv.), the solution was stirred at room temperature for 3 hours. The product was isolated in the usual manner and recrystallized from n-hexane to give 1-(p-toluenesulfonyl)-3-methyl-2-butene (2.16 g, 96.4%), melting point: 71°-72° C.

NMR δ: 1.34(3H), 1.70(3H, 2.42(3H), 3.70 & 3.34(2H), 5.22(1H), 7.30(2H), 7.78(2H).

Elemental analysis (%): Found: C, 64.14; H, 7.06; Calcd. for $C_{12}H_{16}O_2S$: C, 64.25; H, 7.19.

Reference Example 2

According to the procedure of Reference Example 1, trans-1-chloro-3,7-dimethyl-2,6-octadiene (1.8 g, 10.4 m moles) was converted into trans-1-(p-toluenesulfonyl)-3,7-dimethyl-2,6-octadiene (2.82 g, 96.6%), melting point: 44° C.

NMR δ: 1.34(3H), 1.60(3H), 1.70(3H), 2.00 & 2.04(4H), 2.42(3H), 3.70 & 3.34(2H), 5.22(1H), 5.08(1H), 7.30(2H), 7.78(2H)

Elemental analysis (%): Found: C, 69.67; H, 8.42: Calcd. for $C_{17}H_{24}O_2S$: C, 69.82; H, 8.27.

Reference Example 3

According to the procedure of Reference Example 1, trans-farnesyl bromide (2.85 g, 10 m moles) was converted into all trans-1-(p-toluenesulfonyl)-3,7,11-trimethyl-2,6,10-dodecatriene (3.37 g, 93.6%). Colorless oil.

NMR δ: 1.37(3H), 1.61(6H), 1.70(3H), 2.00 & 2.07(8H), 2.46(3H), 3.74 & 3.87(2H), 5.10(2H), 5.20(1H), 7.32(2H), 7.76(2H)

Elemental analysis (%): Found: C, 73.36; H, 8.76: Calcd. for $C_{22}H_{32}O_2S$: C, 73.28; H, 8.95.

Reference Example 4

According to the procedure of Reference Example 1, solanesyl bromide (720 mg, 1 m mole) was converted into solanesyl p-toluene sulfone (728 mg), melting point: 50°–51° C.

NMR δ: 1.34(3H), 1.58(24H), 1.65(3H), 1.98(32H), 2.41(3H), 3.71(2H), 5.07(9H) and 7.26 and 7.70(4H).

Reference Example 5

(5-a) All trans 1-(p-Toluene sulfonyl)-3,7-dimethyl-8-chloro-2,6-octadiene was prepared according to the similar procedures of Examples 1-a) to 1-h) from trans geranyl p-toluene sulfone. NMR: δ1.38(3H), 1.72(3H), 2.03 and 2.10(4H), 2.44(3H), 3.79(2H), 4.00(2H), 5.25(1H), 5.48(1H), and 7.36 and 7.80(4H).

(5-b) Compounds,

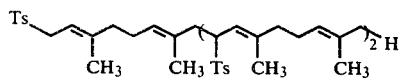

[δ1.24(6H), 1.36(3H), 1.55(6H), 1.61(3H), 1.72(3H), 1.9-2.1(2H), 2.44(3H), 2.88(2H), 3.80(2H), 3.95(2H) 4.90(2H), 5.0-5.3(4H), 7.31(6H), 7.73(6H)] and

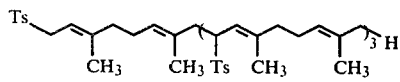

[δ1.24(9H), 1.36(3H), 1.55(9H), 1.61(3H), 1.72(3H), 1.8-2.05(16H), 2.44(12H), 2.9(3H), 3.8(2H), 4.95(3H), 4.90(3H), 5.0-5.4(5H), 7.31(8H), 7.73(8H)], were prepared by the repeated coupling reaction according to the similar procedure of Example 1-i) from geranyl p-toluene sulfone and 1-(p-toluene sulfonyl)-3,7-dimethyl-8-chloro-2,6-octadiene.

EXAMPLE 1

(1-a) In 20% aqueous 1,2-dimethoxyethane (100 ml) was dissolved ubiquinone-7(1.977 g, 3 m moles) and, under cooling at −5° C., crystals of N-bromosuccinimide (590 mg, 3.7 m moles, 1.2 equivalents) were added gradually with stirring. The addition of N-bromosuccinimide was carried out over an hour, after which the mixture was further kept to react under the same conditions for 2 hours. Thereafter, the reaction mixture was diluted with water (200 ml) and extracted with ethyl acetate. The organic layer was washed with water, dried (over sodium sulfate) and concentrated under reduced pressure. The resulting oil (2.280 g) was dissolved in hexane and chromatographed on silica gel [Merck (same hereafter) 200 mesh, 100 g]. Elution with n-hexane-isopropyl ether (2:1) yielded unreacted ubiquinone-7(238 mg). Then, with isopropyl ether, there was obtained VII-dihydro-26′-bromo-27′-hydroxyubiquinone-7(1.542 g, 68%). An orange-yellow oil.

IR(liquid film): 3500(OH), 1650 & 1614(quinone & double bond), 1265 $cm^{-1}$(C-O)

NMR δ: ca. 5.10(6H), 3.99 & 3.97(6H, 20CH₃), 3.22 & 3.14(2H), 2.02(24H), 1.74(3H), 1.61(15H, vinylmethyl), 3.97(1H, quartet, J=6 & 13Hz), 1.34

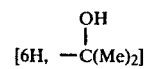

Elemental analysis (%): Found: C, 69.62; H, 8.96: Calcd. for $C_{44}H_{67}O_5Br$: C, 69.91; H, 8.93.

(1-b) In methanol (50 ml) was dissolved VII-dihydro-26′-bromo-27′-hydroxyubiquinone-7(756 mg, 1 m mole). After the solution was cooled to 0° C., potassium carbonate (140 mg, 1.01 equiv.) was added at one time. The mixture was stirred for 4 hours and, after addition of water, the product was extracted with n-hexane. The n-hexane solution was washed with water, dried (Na₂SO₄) and concentrated. By this procedure was obtained VII-dihydro-26′, 27′-epoxyubiquinone-7(672 mg, 99.7%). This product gave a single spot in thin-layer chromatography on silica gel as well as in high-speed liquid chromatography.

IR(liquid film): 1650 & 1612(quinone & double bond), 1265 $cm^{-1}$(C-O)

NMR δ: ca. 5.10(6H), 3.99 & 3.97(3H), 3.22 & 3.14(2H), 2.68(1H, triplet, 6Hz), 2.02(24H), 1.74(3H), 1.60(15H, vinylmethyl), 1.30(3H)

Elemental analysis(%): Found: C, 78.56; H, 9.69: Calcd. for $C_{44}H_{66}O_5$: C, 78.29; H, 9.86.

Mass spectrum: M/e 81, 197, 235, 250, 674(parent peak), 676(M⁺ +2)

(1-c) In 95% ethanol (10 ml) was dissolved VII-dihydro-26′,27′-epoxyubiquinone-7(675 mg, 1 m mole), followed by addition of sodium borohydride (100 mg). The mixture was stirred at room temperature. When the orange-red solution had become colorless, water(50 ml) was added, followed by extraction with isopropyl ether. Usual work-up gave the crude product which was dissolved in dry dimethylformamide (30 ml). Following addition of sodium hydride (50% oily, 240 mg), the mixture was stirred for 5 minutes and, at room temperature, benzyl bromide (350 mg) was added. After one hour, water(50 ml) was added and the product was extracted with n-hexane. The extract was treated in the usual manner to obtain a crude product. This crude product was chromatographed on silica gel (100 mesh, 50 g) and the fraction obtained with n-hexane-isopropyl ether (3:2) was concentrated to give VII-dihydro-26′, 27′-epoxyubiquinol-7 dibenzyl ether (791 mg, 92.3%). Colorless oil.

NMR δ: 7.35(10H), 4.96(4H, —CH₂—), 3.92(6H, 20CH₃), 2.12(3H), 3.36 & 3.28(2H), 5.10(6H), 1.66(3H), 1.58(15H, vinylmethyl), 1.99(24H, —CH₂—), 2.67(1H,

1.28 & 1.25

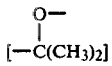

Elemental analysis (%): Found: C, 81.33; H, 11.64: Calcd. for C₅₈H₈₀O₅: C, 81.26; H, 11.58. (1-d) In 10% aqueous 1,2-dimethoxyethane (30 ml) was dissolved VII-dihydro-26′, 27′-epoxyubiquinonol-7 dibenzyl ether (857 mg, 1 m mole). At room temperature, 70% perchloric acid (0.1 ml) was added and the mixture was allowed to stand for 12 hours. The reaction product was treated in the usual manner to obtain a crude product (880 mg). This crude product was chromatographed on silica gel (100 mesh, 50 g). The first fraction obtained with isopropyl ether was discarded and a second fraction obtained with 15% ethyl acetate isopropyl ether was collected. By this procedure was obtained VII-dihydro-26′, 27-dihydroxyubiquinonol-7 dibenzyl ether (865 mg, 98.8%). Colorless oil.

NMR δ: 7.40(10H), 4.98(4H), 3.92(6H, 20CH₃), 2.09(3H), 3.36 & 3.28(2H), 5.10(6H), 1.66(3H), 1.58(15H), 2.00(24H, —CH₂—), 3.34(1H, >C$\underline{H}$-O), 1.16 & 1.13

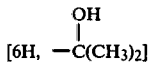

Elemental analysis (%):

Found: C, 79.43; H, 9.66: Calcd. for C₅₈H₈₂O₆: C, 79.59; H, 9.44. (1-e) In a 1:1 mixture (5 ml) of pyridine and acetic anhydride was dissolved VII-dihydro-26′, 27′-dihydroxyubiquinonol-7 dibenzyl ether (438 mg, 0.5 m mole) and the solution was allowed to stand at room temperature for 20 hours. The reaction mixture was poured in 5% hydrochloric acid-ice water (50 ml) and stirred for 30 minutes. The reaction product was extracted with isopropyl ether and the organic layer was washed with water, dried and concentrated. By this procedure was obtained VII-dihydro-26′-acetoxy-27′-hydroxyubiquinol-7 dibenzyl ether (450 mg, 98.3%) as a single-component. Colorless oil.

NMR δ: 7.35(10H), 4.96(4H), 3.93(6H, 20CH₃), 2.10(3H), 3.37 & 3.28(1H), 5.10(6H), 1.66(3H), 1.57(15H, vinylmethyl), 1.98(24H, —CH₂—), 4.84(1H, >C$\underline{H}$OAc), 2.07(3H, Ac), 1.17

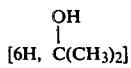

A portion (100 mg) of the monoacetate obtained above was chromatographed on silica gel (100 mesh, 10 g) and elution was carried out with isopropyl ether. The sample obtained by this purification procedure was analyzed.

Elemental analysis (%):

Found: C, 78.43; H, 9.36: Calcd. for C₆₀H₈₄O₇: C, 78.56; H, 9.23. (1-f) In a mixture of dry cyclohexane (20 ml) and dry pyridine (5 ml) was dissolved VII-dihydro-26′-acetoxy-27′-hydroxyubiquinol-7 dibenzyl ether (458 mg, 0.5 m mole). The solution was cooled to 0° C. and a cyclohexane solution (3 ml) of thionyl chloride (120 mg, 2 equiv.) was gradually added. The reaction mixture was gradually warmed to room temperature and followed by the addition of 10% aqueous hydrochloric acid (50 ml), the product was extracted with isopropyl ether. The extract was treated in the usual manner and the resulting crude product was chromatographed on silica gel (100 mesh, 10 g). The fraction first obtained with isopropyl ether was concentrated to give VII-dihydro-26′-acetoxy-27′-ene-ubiquinol-7 dibenzyl ether (437 mg, 97.3%). Colorless oil.

NMR δ: 7.34(10H), 4.95(4H), 3.92(6H, 20CH₃), 2.10(3H), 3.36 & 3.27(2H), 5.10(9H, br.), 1.68(6H, vinylmethyl), 1.57(15H, vinylmethyl), 1.98(24H, —CH₂—), 2.03(3H, Ac)

Elemental analysis (%): Found: C, 79.96; H, 9.10: Calcd. for C₆₀H₈₂O₆: C, 80.13; H, 9.19. (1-g) In 10% aqueous 1,2-dimethoxyethane (10 ml) was dissolved VII-dihydro-26′-acetoxy-27′-ene-ubiquinonol-7 dibenzyl ether (450 mg, 0.5 m mole). At room temperature a 10% aqueous solution of sodium hydroxide (0.4 ml) was added and the mixture was stirred for 6 hours. Thereafter, the reaction mixture was extracted with isopropyl ether and the extract was treated in the usual manner. By this procedure was obtained VII-dihydro-26′-hydroxy-27′-ene-ubiquinol-7 dibenzyl ether as a single product (405 mg, 94.5%). Corless oil.

NMR δ: 7.34(10H), 4.97(4H), 3.94(6H, 20CH₃), 2.11(3H), 3.36 & 3.26(2H), 5.10(8H, br.), 1.68(6H, vinylmethyl), 1.58(15H, vinylmethyl), 2.00(24H, —CH₂—)

Elemental analysis (%): Found: C, 81.29; H, 9.36: Calcd. for C₅₈H₈₀O₅: C, 81.26; H, 9.41. (1-g′) In dry tetrahydrofuran (5 ml) was dissolved VII-dihydro-26′, 27′-epoxyubiquinonol-7 dibenzyl ether (875 mg, 1 m mole) and, at 5° C., the solution was added to a solution (25 ml) of lithium diisopropylamide (500 mg, 5 equiv.) in dry tetrahydrofuran. The reaction was conducted under nitrogen gas for 10 hours. To the reaction mixture was added 2% aqueous hydrochloric acid (50 ml) and the product was extracted with isopropyl ether. The resulting crude product was chromatographed on silica gel (100 mesh, 50 g) and after a first fraction containing a small amount of undesired impurity eluted with isopropyl ether was discarded, a subsequent fraction was collected and concentrated. By this procedure was obtained VII-dihydro-26′-hydroxy-27′-ene-ubiquinonol-7 dibenzyl ether (756 mg, 86.4%). (1-h) In dry tetrahydrofuran (10 ml) was dissolved VII-dihydro-26′-hydroxy-27′-ene-ubiquinol-7 dibenzyl ether (429 mg, 0.5 m mole), followed by addition of dry tetrahydrofuran (2 ml) containing thionyl chloride (120 mg, 2 equiv.) at room temperature. After 2 hours, water (50 ml) was added to the reaction mixture and the product was extracted with isopropyl ether. The extract was treated in the usual manner and the resulting crude product was chromatographed on silica gel (100 mesh, 3 g). A first fraction eluted with n-hexane-isopropyl ether (1:1) was concentrated. By the above procedure was obtained 28′-chloroubiquinol-7 dibenzyl ether (430 mg, 98.3%). Colorless oil.

NMR δ: 1.60(15H, vinylmethyl), 1.68(3H), 1.72(3H), 2.02(24H, —CH₂—), 2.12(3H), 3.30 & 3.36(2H), 3.94(6H, 20CH₃), 3.98(2H, —CH₂Cl), 4.96(4H), 5.10(6H), 5.50(1H), 7.40(10H)

Elemental analysis (%): Found: C, 79.21; H, 8.96: Calcd. for $C_{58}H_{79}O_4Cl$: C, 79.55; H, 9.09. (1-i) In a solvent mixture of dry tetrahydrofuran (3 ml) and dry hexamethyl phosphoramide (1 ml) was dissolved trans-1-(p-toluenesulfonyl)-3,7,11-trimethyl-2,6,10-dodecatriene (216 mg, 0.6 m mole). Then, under cooling at −78° C. and under nitrogen gas, a solution of n-butyllithium in n-hexane (10% W/V, 0.39 ml, 1.01 equiv.) was added, whereupon the reaction mixture became orange-red. Then, a solution (3 ml) of 28′-chloroubiquinol-7 dibenzyl ether (440 mg, 0.5 m mole) in dry tetrahydrofuran was gradually added and the reaction mixture was stirred. After the addition of the chloride solution was completed, the reaction temperature was gradually warmed to room temperature over a period of about 2 hours. During the reaction, the colored solution faded. After the reaction, acetic acid (0.5 ml) and water (50 ml) were added and the product was extracted with isopropyl ether. The extract was treated in the usual manner to obtain a crude product. The crude product was chromatographed on silica gel. Elution with a 3:1 mixture of n-hexane and isopropyl ether gave a small amount of undesired mixtures which was discarded, subsequent fractions were collected and concentrated. By this procedure was obtained 29′-(p-toluenesulfonyl)ubiquinol-10 dibenzyl ether (442 mg, 73.6%). Colorless oil.

NMR δ: 1.22(3H), 1.58(8-Me), 1.67(3H), 1.98(—CH₂—), 2.10(3H), 2.40(3H), 3.26 & 3.36(2H), 3.74(1H,>CHSO₂—), 3.92(6H, 20CH₃), 5.10(10H, br.), 7.30 (2H), 7.40(10H), 7.75(2H)

Elemental analysis(%): Found: C, 80.32; H, 9.36: Calcd. for $C_{80}H_{110}O_6S$: C, 80.08; H, 9.24. (1-j) In ethylamine (5 ml) was dissolved 29′-(p-toluenesulfonyl)ubiquinol-10 dibenzyl ether (120 mg, 0.1 m mole). With stirring under nitrogen gas and cooling at −30° C., lithium (10 mg) was added. The reaction mixture was gradually warmed to −20° C. and, after the reaction mixture had turned blue, the reaction was further continued to react under the same conditions for 10 minutes. Then, the ethylamine was thoroughly removed under a reduced pressure and a low temperature and tetrahydrofuran (30 ml) containing 5% of acetic acid was added to the residue. To this solution was added a 10% aqueous solution of ferric chloride (1.0 ml) and the mixture was stirred at room temperature for 2 hours. Following addition of water (100 ml), the product was extracted with isopropyl ether. The extract was treated in the usual manner to obtain a crude product (103 mg). This crude product was chromatographed on silica gel (30 g) and eluted with n-hexane-isopropyl ether (3:1). After removal of a first colorless fraction, subsequent fractions were concentrated to give ubiquinone-10 (62 mg, 72%), melting point: 48°–49° C., orange-yellow crystals.

NMR δ: 1.59(9-CH₃), 1.67(3H), 1.73(3H), 2.01(36H, —CH₂—), 3.16 & 3.22(2H), 3.98 & 3.99(6H, 20CH₃), 5.10(10H)

This product was identified with naturally-occurring ubiquinone-10 by mixture-melting point measurement, NMR spectrum, silica gel TLC, high-speed liquid chromatography (silica gel) and mass spectrum.

EXAMPLE 2

(2-a) In ethanol (10 ml) was dissolved VII-dihydro-26′,27′-epoxyubiquinone-7(675 mg, 1 m mole) and, after the solution was cooled to 10° C., sodium borohydride (50 mg) was added. When the reaction mixture had become colorless, isopropyl ether and water were added to bring the product into the organic layer. The product was isolated in the usual manner and the crude product was dissolved in dimethylformamide(20 ml). The solution was cooled to 5° C. under nitrogen gas, followed by addition of sodium hydride (50% oil dispersion, 125 mg, 2.5 m moles), stirred well under the same conditions. Then, a solution (5 ml) of chloromethyl methyl ether (201 mg, 2.5 m moles) in methylene chloride was added. After 30 minutes, isopropyl ether and water were added to the reaction mixture. The crude product was isolated in the usual manner. The crude product was chromatographed on silica gel (30 g) and elution was first carried out with n-hexane to remove the oil originating from the sodium hydride. A second fraction obtained with a 1:1 mixture of n-hexane and isopropyl ether was concentrated, whereupon VII-dihydro-26′,27′-epoxyubiquinol-7 bis-(methoxymethyl)ether (743 mg, 97.1%) was obtained. Colorless oil.

NMR δ: 1.25(3H), 1.29(3H), 1.60(15H), 1.77(3H), 2.00 (24H), 2.18(3H), 2.68(1H), 3.34 & 3.44(2H), 3.57 (6H), 3.85(6H), 5.05(4H), 5.0–5.3(6H)

Elemental analysis (%): Found: C, 75.56; H, 9.88: Calcd. for $C_{48}H_{76}O_7$: C, 75.35; H, 10.01. (2-b) VII-dihydro-26′,27′-epoxyubiquinonol-7 bis-(methoxymethyl)ether (383 mg, 0.5 m mole) was treated as in Example 1-g′) and the reaction product was isolated and purified. By the above procedure was obtained VII-dihydro-26′-hydroxy-27′-ene-ubiquinol-7 bis(methoxymethyl)-ether (320 mg, 83.5%). Colorless oil.

NMR δ: 1.59(15H), 1.74(6H), 2.00(24H), 2.17(3H), 3.32 & 3.42(2H), 3.57(6H), 3.84(6H) 4.03(1H), 4.89 & 4.95(2H), 5.05(4H), 5.0–5.3(6H)

Elemental analysis (%): Found: C, 75.46; H, 10.32: Calcd. for $C_{48}H_{76}O_7$: C, 75.35; H, 10.01. (2-c) In dimethylformamide (10 ml) was dissolved VII-dihydro-26′-hydroxy-27′-ene-ubiquinol-7 bis(methoxymethyl)-ether (300 mg, 0.39 m mole) and the solution was cooled to 5° C. To this solution was added a solution (2 ml of thionyl chloride (94 mg, 2 equiv.) in methylene chloride. The mixture was reacted under the same conditions for 2 hours and the resulting product was purified in the usual manner. By the above procedure was obtained 28′-chloroubiquinol-7 bis(methoxymethyl)ether (268 mg, 87%). Colorless oil.

NMR δ: 1.59(15H), 1.68(3H), 1.72(3H), 2.02(24H), 2.17(3H), 3.32 & 3.42(2H), 3.57(6H), 3.84(6H), 3.98(2H), 5.50(4H), 5.0–5.3(6H), 5.50(1H)

Elemental analysis (%): Found: C, 73.36; H, 9.38: Calcd. for $C_{48}H_{75}O_6Cl$: C, 73.57; H, 9.65. (2d) 28′-Chloroubiquinol-7 bis(methoxymethyl)ether (100 mg, 0.128 m mole) was allowed to react with trans-1-(p-toluenesulfonyl)-3,7,11-trimethyl-2,6,10-dodecatriene (55 mg, 1.2 equiv.) in the same manner as Example 1-i) and the reaction product was isolated and purified. This procedure provided 29′-(p-toluenesulfonyl)ubiquinol-10 bis(methoxymethyl)ether (98 mg, 69%). Colorless oil.

NMR δ: 1.23(3H), 1.58(8-Me), 1.67(3H), 1.98(13CH₂—), 2.17(3H), 3.32 & 3.42(2H), 3.74(1H,>CHSO₂—), 3.57(6H), 3.84(6H), 5.0–5.3(10H), 7.30(2H), 7.75(2H)

Elemental analysis (%): Found: C, 76.24; H, 9.71: Calcd. for $C_{70}H_{106}O_8S$: C, 75.90; H, 9.65. (2e) In ethylamine (5 ml) was dissolved 29'-(p-toluenesulfonyl)ubiquinol-10 bis(methoxymethyl)ether (90 mg, 0.08 m mole). The solution was cooled to −30° C. with stirring under nitrogen gas and lithium (10 mg) was added. The reaction temperature was gradually warmed to −20° C. and after the reaction mixture had turned blue, it was further continued to react under the same conditions for 10 minutes. After the reaction, the ethylamine was removed under reduced pressure and the residue was treated with a mixture of acetic acid (0.1 ml) and isopropyl ether (50 ml). This solution was washed with water and concentrated. The residue was chromatographed on silica gel (10 g) and elution was carried out with n-hexane-isopropyl ether (3:1). The eluate was concentrated to obtain ubiquinol-10 bis(methoxymethyl)ether (54 mg, 71%). Colorless oil.

NMR δ: 1.60(9-Me), 1.68(3H), 1.72(3H), 2.02(18—CH₂—), 2.17(3H), 3.32 & 3.42(2H), 3.57(6H), 3.84(6H), 5.04(4H), 5.0–5.2(10H).

Elemental analysis (%): Found: C, 79.22; H, 10.68: Calcd. for $C_{63}H_{100}O_6$: C, 79.35; H, 10.57. (2-f) In 10% aqueous 1,2-dimethoxyethane (5 ml) was dissolved ubiquinol-10 bis(methoxymethyl)ether (50 mg). At room temperature, 70% perchloric acid (0.1 ml) was added and the mixture was allowed to stand in the dark place. To this solution was added ferric chloride (20 mg) and the mixture was stirred under the same conditions for 2 hours. n-Hexane and water were added to the reaction mixture to bring the product into the n-hexane layer, which was washed with water and concentrated. The residue was chromatographed on silica gel (5 g) and elution was carried out with n-hexane-isopropyl ether (3:1). The above procedure provided ubiquinone-10.

EXAMPLE 3

(3-a) By a procedure similar to that of Example 1-d), VII-dihydro-26',27'-epoxyubiquinone-7 (1.348 g, 2 m moles) was treated in the presence of perchloric acid (70%, 0.1 ml) to give VII-dihydro-26',27'-dihydroxyubiquinone-7(1.312 g, 94.7%). Orange-yellow oil.

IR(liquid film): ca. 3400(OH), 1650 & 1612(quinone & double bond), 1265 cm⁻¹(C-O)

NMR δ: ca. 5.10(6H), 3.99 & 3.97(6H, 20CH₃), 2.02 & 2.04(24H, —CH₂—), 1.74(3H), 1.60(15H, vinylmethyl), 3.34(1H, quartet, J=3 & 9Hz), 1.16 & 1.20

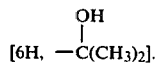

Elemental analysis (%): Found: C, 76.08; H, 10.12: Calcd. for $C_{44}H_{68}O_6$: C, 76.26; H, 9.89. (3-b) In acetic acid (40 ml) was dissolved VII-dihydro-26',27'-epoxyubiquinone-7(674 mg, 1 m mole), followed by addition of sodium acetate(4 g). The mixture was heated at 65° C. under nitrogen gas for 3 hours. The reaction mixture was then cooled and followed by addition of water (100 ml), and the product was extracted with isopropyl ether. The organic layer was washed with water, dried (Na₂SO₄) and concentrated. The residue was chromatographed on silica gel (50 g, 100 mesh). The first fraction eluted with isopropyl ether was discarded and the subsequent fraction was concentrated to give VII-dihydro-26'-acetoxy-27'-hydroxyubiquinone-7(525 mg, 78%). Orange-red oil.

IR(liquid film): 3450(OH), 1735(OAc), 1650 & 1612 (quinone & double bond), 1265cm⁻¹(C-O)

NMR δ: ca. 5.10(6H), 3.99 & 3.97(6H, 20CH₃), 3.22 & 3.15(2H), 2.04(24H, —CH₂—), 1.74(3H), 1.61(15H, vinylmethyl), 2.10(OAc), 4.84(1H), 1.20

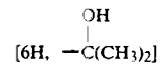

Elemental analysis (%): Found: C, 75.27; H, 9.77: Calcd. for $C_{46}H_{70}O_7$: C, 75.16; H, 9.60. (3-b') VII-Dihydro-26',27'-dihydroxyubiquinone-7(693 mg, 1 m mole) was subjected to a similar procedure to that of Example 1-e) to give VII-dihydro-26'-acetoxy-27'-hydroxyubiquinone-7(699 mg, 95.2%). (3-c) By a procedure similar to that of Example 1-f), VII-dihydro-26'-acetoxy-27'-hydroxyubiquinone-7(735 mg, 1 m mole) was treated to give VII-dihydro-26'-acetoxy-27'-ene-ubiquinone-7 (687 mg, 95.8%). Orange-yellow oil.

IR(liquid film): 1735(OAc), 1650 & 1613(quinone & double bond), 1265 & 1235cm⁻¹(C-O)

NMR δ: ca. 3.10(6H), 5.00(1H), 4.89 & 4.95(2H, =CH₂), 3.99 & 3.97(6H, 20CH₃), 3.22 & 3.15(2H), 2.04 & 2.02(24H), 1.74(6H), 1.61(15H, vinylmethyl), 2.05(OAc)

Elemental analysis (%): Found: C, 76.98; H, 9.42: Calcd. for $C_{46}H_{68}O_6$: C, 77.05; H, 9.56. (3-d) By a procedure similar to that of Example 1-g), VII-dihydro-26'-acetoxy-27'-ene-ubiquinone-7(717 mg), 1 m mole) was treated to give VII-dihydro-26'-hydroxy-27'-ene-ubiquinone-7(653 mg, 96.9%). Orange-yellow oil.

IR(liquid film): 3400(OH), 1650 & 1612(quinone & double bond), 1265cm⁻¹(C-O)

NMR δ: ca. 5.10(6H), 3.99 & 3.97(6H, 20CH₃), 3.22 & 3.15(2H), 2.02(24H), 1.74(6H, vinylmethyl), 1.61 (15H, vinylmethyl), 4.03(1H,>CHOH), 4.94 & 4.83 (2H, =CH₂)

Elemental analysis (%): Found: C, 78.36; H, 9.73: Calcd. for $C_{44}H_{66}O_5$: C, 78.29; H, 9.86. (3-e) By a procedure similar to that of Example 1-h), VII-dihydro-26'-hydroxy-27'-ene-ubiquinone-7(693 mg, 1 m mole) was treated to give 28'-chloroubiquinone-7 (587 mg, 84.7%). Orange-red oil.

IR(liquid film): 1650 & 1613(quinone & double bond), 1265 cm⁻¹(C-O)

NMR δ: ca. 5.10(6H), 3.98 & 3.99(6H, 20CH₃), 3.22 & 3.15(2H), 2.02(24H, —CH₂—), 1.74(6H, vinylmethyl), 1.61(15H, vinylmethyl), 5.52(1H, triplet), 3.99 (2H, —CH₂-Cl).

Elemental analysis (%): Found: C, 76.07; H, 9.33: Calcd. for $C_{44}H_{65}O_4Cl$: C, 76.21; H, 9.45. (3-f) 28'-chloroubiquinone-7(700 mg, 1 m mole) in dimethyl formamide (10 ml) was allowed to react with sodium p-toluene sulfinate dihydrate (300 mg, 1.2 m moles) at room temperature over night. The product was isolated in the usual work up to give 28'-(p-toluene sulfonyl)-ubiquinone-7. The sulfonyl compound, without further purification, was dissolved in ethanol (10 ml) and reduced with sodium borohydride (100 mg) at room temperature. After the reaction was completed, the product was isolated in the usual manner to give the corresponding hydroquinone. The hydroquinone was benzylated with benzyl bromide and sodium hydride at room temperature. The reaction mixture was worked up in the usual manner to give 28'-(p-toluene sulfonyl)-ubiquinol dibenzyl ether (825 mg).

δ: 1.60(18H), 1.68(3H), 2.02(24H), 2.12(3H), 2.42(3H), 3.30 and 3.36(2H), 3.57(2H), 3.93(6H), 4.96(4H), 5.10(7H), 7.40(10H), 7.21 and 7.64(4H). (3-g) 26'-Hydroxy-27'-ene-ubiquinone-7 (340 mg, 0.5 m mole) was dissolved in ethanol (10 ml) at room temperature and reduced with sodium borohydride (50 mg). The resulting product, after isolation in the usual manner, was benzylated in dimethylformamide with benzyl bromide (180 mg) and sodium hydride (100 mg) to give 26'-hydroxy-27'-ene-ubiquinol-7 dibenzyl ether (410 mg) as a colorless oil. The NMR data is the same as described in Example (1-g).

EXAMPLE 4

(4-a) By a procedure similar to that of Example (1-i), trans-1-(p-toluenesulfonyl)-3,7-dimethyl-2,6-octadiene (175 mg, 1.2 equiv.) was allowed to react with 28'-chloroubiquinol-7 dibenzyl ether (440 mg, 0.5 m mole) to give 29'-(p-toluenesulfonyl)ubiquinol-9 dibenzyl ether (452 mg). Colorless oil.

NMR δ: 1.24(3H), 1.60(18H), 1.68(6H), 2.00(30H), 2.12 (3H), 2.43(3H), 3.24(1H), 3.36(1H), 3.74(1H), 3.93(6H), 4.96(4H), ca.5.10(9H), 7.3–7.6(12H), 7.70(2H)

Elemental analysis (%): Found: C, 79.32; H, 9.16: Calcd. for $C_{75}H_{102}O_6S$: C, 79.60; H, 9.08.

(4-b) By a procedure similar to that of Example (1-j), 29'-(p-toluenesulfonyl)ubiquinol-9 dibenzyl ether (113 mg, 0.1 m mole) was treated to give ubiquinone-9 (62 mg, 78%). melting point: 43°–44° C., orange-yellow crystals.

NMR δ: 1.60(8-CH$_3$), 1.67(3H), 1.73(3H), 2.01(28H), 3.16 & 3.22(2H), 3.98 & 3.99(6H), 5.10(9H)

This product was directly compared and identified with natural ubiquinone-9 by mixture-melting point measurement, NMR spectrum, silica gel TLC, high-speed liquid chromatography (silica gel) and mass spectrum.

EXAMPLE 5

(5-a) By a procedure similar to that of Example (1-i), 1-(p-toluenesulfonyl)-3-methyl-2-butene(134 mg, 1.2 equiv.) was allowed to react with 28'-chloroubiquinol-7 dibenzyl ether (440 mg, 0.5 m mole) to give 29'-(p-toluenesulfonyl)-ubiquinol-8 dibenzyl ether (448 mg). Colorless oil.

δ: 1.18(3H), 1.60(18H), 2.00(26H), 2.12(3H), 3.24(1H), 3.36(1H), 3.73(1H), 3.93(6H), 4.96(4H), ca.5.10 (8H), 7.3–7.6(12H), 7.70(2H)

Elemental analysis (%): Found: C, 79.22; H, 8.85: Calcd. for $C_{70}H_{94}O_6S$: C, 79.05; H, 8.91.

(5-b) By a procedure similar to that of Example (1-j), 29'-(p-toluenesulfonyl)ubiquinol-8 dibenzyl ether (106 mg, 0.1 m mole) was treated to give ubiquinone-8 (54 mg, 74%), melting point: 36°–37° C., orange-yellow crystals.

δ: 1.59(7-CH$_3$), 1.67(3H), 1.73(3H), 2.01(28H), 3.16 & 3.22(2H), 3.98 & 3.99(6H), 5.10(9H)

This product was directly compared and identified with natural ubiquinone-8 by mixture-melting point measurement, NMR spectrum, silica gel TLC, high-speed liquid chromatography (silica gel) and mass spectrum.

EXAMPLE 6

According to the procedures of Examples (2-a), (2-b) and (2-c), ubiquinol-1 bis-(ethoxymethyl)ether [δ 1.20(3H), 1.65(3H), 1.72(3H), 2.14(3H), 3.34(2H), 3.76(2H), 3.80 (6H), 5.04(3H)] was converted into 4'-bromo-ubiquinol-1 bis-(ethoxymethyl)ether. δ 1.20(3H), 1.89(3H), 2.13(3H), 3.34(2H), 3.96(2H), 5.06(4H), 5.46(1H).

EXAMPLE 7

Ubiquinone-10 was prepared according to the similar procedures of Examples (2-d), (2-e) and (2-f) from 4'-bromo-ubiquinol-1 bis-(ethoxymethyl)ether and solanesyl p-toluene sulfone.

EXAMPLE 8

(8-a) In a solvent mixture of 1,2-dimethoxyethane (6 ml) and water (1.2 ml) was dissolved trans-2-methyl-3-(3',7'-dimethyl-2',6'-octadienyl)-1,4-dimethoxynaphthalene (500 mg, 1.5 m moles). After the solution was cooled to −10° C., N-bromosuccinimide (320 mg, 1.8 m moles) was gradually added. After the addition, the mixture was stirred under the same conditions for 3 hours. To this reaction mixture was added n-hexane and the organic layer was washed with water, dried and concentrated under reduced pressure. The crude product was purified on silica gel (10 g) to give the bromohydrin compound (400 mg, 78%).

NMR δ: 1.27(6H), 1.82(3H), 2.36(3H), 3.55(2H), 3.80(3H), 3.83(3H), 3.97(1H), 5.20(1H), 7.23–7.56(2H), 7.82–8.16(2H).

(8-b) In a mixture of methanol (30 ml), 1,2-dimethoxyethane (10 ml) and water (5 ml) was dissolved trans-2-methyl-3-(6'-bromo-7'-hydroxy-3',7'-dimethyl-2'-octenyl)-1,4-dimethoxynaphthalene(4.35 g, 10 m moles) and the solution was cooled to 0° C. To this added potassium hydroxide (3 g, 56 m moles) and after the reaction temperature was elevated to room temperature, the mixture was continued to stir for 30 minutes. The reaction mixture was concentrated under reduced pressure and extracted 3 times with benzene. The extract was treated in the usual manner to obtain the desired epoxy-compound (3.45 g, 97.5%), Colorless oil.

NMR δ: 1.24(6H), 1.82(3H), 2.36(3H), 2.66(1H), 3.55(2H), 3.80 & 3.83(6H), 5.20(1H), 7.23–7.56(2H), 7.82–8.16 (2H).

(8-b') In methylene chloride (30 ml) was dissolved trans-2-methyl-3-(3',7'-dimethyl-2',6'-octadienyl)-1,4-dimethoxynaphthalene (3.38 g) and the solution was cooled to 0° C. Then, m-chloroperbenzoic acid (85% purity, 2.2 g, 1.1 equiv.) was gradually added. After the addition was completed, the mixture was further stirred under the same conditions for 3 hours. The reaction mixture was washed with an aqueous solution of sodium carbonate and the organic layer was washed with water, dried (Na$_2$SO$_4$) and concentrated under reduced pressure. The concentrate was purified by chromatography on silica gel to give the desired epoxy-compound (3.15 g, 88.9%).

(8-c) In 10% aqueous 1,2-dimethoxyethane (50 ml) was dissolved trans-2-methyl-3-(6',7'-epoxy-3',7'-dimethyl-2'-octenyl)-1,4-dimethoxynaphthalene (3.54 g, 10 m moles). At room temperature, perchloric acid (70%, 0.2 ml) was added and the mixture was allowed to stand for 5 hours. To this reaction mixture was added water and the product was extracted with isopropyl ether. The extract was treated in the usual manner. By the above procedure was obtained trans-2-methyl-3-(6',7'-dihydroxy-3',7'-dimethyl-2'-octenyl)-1,4-dimethoxynaphthalene (3.68 g, 98.9%). This diol (3.68 g) was dissolved in pyridine (10 ml) and acetic anhydride (30 ml) and the solution was allowed to stand at room temperature overnight. The product was worked up in the usual manner to isolate trans-2-methyl-3-(6'-acetoxy-7'-hydroxy-3',7'-dimethyl-2'-octenyl)-1,4-dimethoxynaphthalene (3.73 g, 89.8%). Colorless oil.

NMR δ: 1.18(6H), 1.80(3H), 2.02(3H), 2.27(3H), 3.52(2H), 3.83(6H), 4.82(1H), 5.18(1H), 7.26–7.50(2H), 7.80–8.12(2H)

(8-d) This monoacetate (3.2 g, 7,7 m moles) was dissolved in benzene (45 ml) and pyridine (45 ml) and the solution was cooled to −15° C. To this was added thionyl chloride (1.5 ml, 21 m moles) and the mixture was stirred at that temperature for 20 minutes. To the reaction mixture was added a 2% aqueous solution of sodium hydrogen carbonate, followed by extraction with benzene. The organic layer was washed with a saturated aqueous solution of sodium chloride, dried over anhydrous sodium sulfate and concentrated under reduced pressure. The residue was chromatographed on silica gel (80 g) using methylene chloride for elution to give trans-3-(6'-acetoxy-3',7'-dimethyl-2',7'-octadienyl)-1,4-dimethoxy-2-methylnaphthalene (2.1 g, 68%). Colorless oil.

IR(liquid film): 1735(OAc), 1653, 1594 cm$^{-1}$

NMR δ: 1.66(3H), 1.80(3H), 2.04(3H), 2.38(3H), 3.54(2H), 3.82(6H), 4.85(2H), 5.05(1H), 7.2–7.6(2H), 7.8–8.2 (2H).

(8-e) In methanol (50 ml) and 1,2-dimethoxyethane (15 ml) was dissolved trans-3-(6'-acetoxy-3',7'-dimethyl-2',7'-octadienyl)-1,4-dimethoxy-2-methylnaphthalene (2.8 g, 7 m moles), followed by addition of 1 N aqueous potassium hydroxide (10 ml). The mixture was stirred at room temperature for 2 hours. To this reaction mixture was added benzene (100 ml) and the water layer was separated out. The benzene layer was then washed with a saturated aqueous solution of sodium chloride, dried over anhydrous sodium sulfate and concentrated under reduced pressure. The resulting oily residue was dissolved in dry tetrahydrofuran (100 ml), and the solution was cooled to −20° C. To this was added thionyl chloride (2.5 ml, 42 m moles) and the mixture was allowed to stand at −15° C. for 18 hours. The reaction mixture was concentrated under reduced pressure and the residue was dissolved in benzene (100 ml). The solution was then washed with sodium hydrogen carbonate, water and saturated aqueous solution of sodium chloride in the order mentioned. The benzene layer was dried (Na$_2$SO$_4$) and concentrated. The residue was chromatographed on silica gel (30 g) using methylene chloride to give trans-3-(3',7'-dimethyl-8'-chloro-2',7'-octadienyl)-1,4-dimethoxy-2-methylnaphthalene (1.7 g, 68%). Colorless oil.

IR(liquid film): 2890, 1593, 1351 cm$^{-1}$

NMR δ: 1.66(3H), 1.86(3H), 2.38(3H), 3.62(2H), 3.82(6H), 3.92(2H), 5.10(1H), 5.52(1H), 7.60–7.30(2H), 7.90–8.30(2H).

(8-f) In dry tetrahydrofuran (20 ml) was dissolved trans-1-phenylthio-3,7-dimethyl-2,6-octadiene (650 mg, 2.6 m moles) and the solution was cooled to −78° C. Under nitrogen gas, a 15% solution of n-butyllithium in hexane (W/W %, 1.6 ml, 2.6 m moles) was added to the above solution with stirring for 2 hours. Then, a solution of trans 3-(3',7'-dimethyl-8'-chloro-2',6'-octadienyl)-1,4-dimethoxy-2-methylnaphthalene (0.7 g, 2 m moles) in dry tetrahydrofuran (5 ml) was added to the above reaction mixture under the same conditions. The reaction was conducted for 40 minutes, at the end of which time it was terminated by the addition of a 1:1 mixture (2 ml) of methanol and ether. To this was added water and the product was extracted with ether. The extract was treated in the usual manner. The resulting product was chromatographed on silica gel (20 g) using n-hexane containing 8% of ether for elution to obtain 9'-phenylthio menaquinol-4 dimethyl ether (1.0 g, 88%).

IR (liquid film): 2830, 1590, 1350 cm$^{-1}$

NMR δ: 1.34(3H), 1.56(6H), 1.68(3H), 1.84(3H), 2.38(3H), 2.01(—CH$_2$—), 3.58(2H), 3.82(6H), 4.80–5.36(4H), 7.18–7.60(7H), 7.90–8.18(2H).

(8-g) Dry ethylamine (120 ml) was cooled to −78° C. and fine metal lithium(0.7 g) was added. The temperature was elevated to −50° C. to −40° C. and the mixture was stirred for 40 minutes. The blue reaction mixture was obtained and cooled to −78° C. To the blue solution was gradually added a solution (30 ml) of 9'-phenylthiomenaquinol-4-dimethyl ether (1.13 g, 2 m moles) in dry tetrahydrofuran. After the dropwise addition had been completed, the mixture was stirred at −78° C. for 15 minutes. The reaction was terminated by the addition of 3-hexine (2 ml). To this reaction mixture was added methanol (5 ml) and the solvent was distilled off under reduced pressure. Following addition of n-hexane and water, the organic layer was washed with water, dried (Na$_2$SO$_4$) and concentrated. The residue was chromatographed on silica gel (20 g) using 8% ether-hexane for elution to obtain 5,8-dihydromenaquinol-4 dimethyl ether (650 mg, 73%). Colorless oil.

IR(liquid film): 2820, 1320 cm$^{-1}$

NMR δ: 1.60(9H), 1.67(3H), 1.78(3H), 2.00 & 2.03(12H, —CH$_2$—), 2.19(3H), 3.35(4H), 3 37(2H), 3.68(6H, 2OCH$_3$), 5.00–5.20(4H), 5.90(2H).

(8-h) In benzene (2 ml) was dissolved 5,8-dihydromenaquinol-4 dimethyl ether (43 mg), followed by addition of 2,3-dichloro-5,6-dicyanobenzoquinone (21 mg). The mixture was warmed at 50° C. for 1 hour. The reaction mixture was chromatographed on alumina (2 g) and elution with benzene to give menaquinol-4 dimethyl ether (40 mg, 93%).

NMR δ: 1.60(9H), 1.67(3H), 1.85(3H), 1.98 & 2.02(12H), 2.38(3H), 3.58(2H), 3.82(6H), 5.00–5.20(4H), 7.30–7.45(2H), 7.90–8.10(2H).

(8-i) In dioxane (20 ml) and ether (20 ml) was dissolved menaquinol-4 dimethyl ether (474 mg, 1 m mole) and the solution was cooled to −15° C. To this solution was added silver (II) oxide (800 mg), further followed by addition of 6.4 N-nitric acid (0.8 ml) and water (0.1 ml). The reaction was conducted under the same conditions with stirring. To the reaction mixture was added n-hexane and the organic layer was washed with water, dried (Na$_2$SO$_4$) and concentrated. The residue was chromatographed on silica gel (10 g) and elution with benzene to obtain menaquinone-4 (257 mg, 57.9%), melting point: 35°–37° C.

IR(liquid film): 2850, 1661, 1620, 1598, 1300 cm$^{-1}$

NMR δ: 1.58(9H), 1.67(3H), 1.79(3H), 1.98 & 2.02(12H), 2.20(3H), 3.34 & 3.40(2H), 4.90–5.20(4H), 7.60–7.70(2H), 8.02–8.12(2H).

EXAMPLE 9

In dioxane (10 ml) and ether (10 ml) was dissolved 5,8-dihydromenaquinol-4 dimethyl ether and the solution was cooled to −15° C. To this solution was added silver (II) oxide (800 mg), followed by dropwise addition of 6,4 N-nitric acid (0.8 ml). To this solution was added water (0.1 ml) and the mixture was stirred at −15° C. for 5 minutes. To the reaction mixture was added n-hexane and the product was extracted, isolated and purified in the usual manner. By the above procedure was obtained 5,8-dihydromenaquinone-4(120 mg, 64%). Yellow oil.

IR(liquid film): 2820, 1647, 1620, 1300 cm$^{-1}$.

NMR δ: 1.60(9H), 1.68(3H), 1.76(3H), 2.02(15H, —CH$_3$ & —CH$_2$—), 3.06(2H), 3.20(2H), 5.0–5.2(4H), 5.80(2H).

EXAMPLE 10

(10-2) Reaction of trans-1-phenylthio-3,7,11-trimethyl-2,6,10-dodecatriene (822 mg, 2.6 m moles) and trans-3-(3',7'-dimethyl-8'-chloro-2',6'-octadienyl)-1,4-dimethoxy-2-methylnaphthalene (0.7 g, 2 m moles) were carried out by the similar procedure as described in Example (8-f) and usual work-up gave 9'-phenylthiomenaquinol-5 dimethyl ether (550 mg, 84.5%).

IR(liquid film): 2830, 1590, 1352 cm$^{-1}$

NMR δ: 1.32(3H), 1.56(9H), 1.68(3H), 1.84(3H), 2.38(3H), 2.02(—CH$_2$—), 3.58(2H), 3.82(6H), 4.83–5.36(5H), 7.18–7.60(7H), 7.90–8.18(2H).

(10-b) 9'-Phenylthio-menaquinol-5 dimethyl ether (1.27 g, 2 m moles) was subjected to reductive desulfurization as in Example (8-g) to obtain 5,8-dihydromenaquinol-5 dimethyl ether (827 mg, 76%). Colorless oil.

IR(liquid film): 2820, 1320 cm$^{-1}$

NMR δ: 1.61(12H), 1.67(3H), 1.76(3H), 2.01(16H), 2.21(3H), 3.36(6H), 3.67(6H), 4.90–5.30(5H), 5.92(2H).

(10-c) 5,8-Dihydromenaquinol-5 dimethyl ether (55 mg, 0.1 m mole) was treated as described in Example (8-h) to obtain menaquinol-5 dimethyl ether (51 mg, 92%). Colorless oil.

NMR δ: 1.60(12H), 1.67(3H), 1.85(3H), 1.98 & 2.02(16H), 2.38(3H), 3.57(2H), 3.82(6H), 5.00–5.20(5H), 7.30–7.45(2H), 7.90–8.10(2H).

(10-d) Menaquinol-5 dimethyl ether (542 mg, 1 m mole) was treated as described in Example (8-i) to obtain menaquinone-5 (286 mg, 55.9%). Yellow crystals, melting point: 43°–44° C.

NMR δ: 1.59(12H), 1.67(3H), 1.79(3H), 1.98 & 2.02(16H), 2.20(3H), 3.34 & 3.40(2H), 4.90–5.20(5H), 7.60–7.70(2H), 8.02–8.12(2H)

EXAMPLE 11

5,8-Dihydromenaquinol-5 dimethyl ether (272 mg, 0.5 m mole) was treated as described in Example 9. Usual work-up gave 5,8-dihydromenaquinone-5 (167 mg, 62%).

IR(liquid film): 2820, 1647, 1620, 1300 cm$^{-1}$

NMR δ: 1.61(12H), 1.68(3H), 1.76(3H), 2.02(19H, —CH$_3$ & —CH$_2$—), 3.06(2H), 3.20(2H), 5.0–5.2(5H), 5.80(2H)

EXAMPLE 12

(12-a) In dichloromethane (100 ml) was dissolved 1,4-dimethoxy-2,3,5-trimethyl-6-(3',7'-dimethyl-2',6'-octadienyl)benzene (8.0 g, 25 m moles) and the solution was cooled to −20° C.

To this solution was dropwise added a solution (200 ml) of m-chloroperbenzoic acid (70% pure, 6.1 g, 25 m moles) in methylene chloride (200 ml). Following this dropwise addition, the mixture was stirred at −20° C. for another hour. The reaction mixture was washed with 10% aqueous potassium carbonate and, then, with water, followed by drying and concentration. By the above procedure was obtained trans-1,4-dimethoxy-2,3,5-trimethyl-6-(3',7'-dimethyl-6',7'-epoxy-2-octenyl)-benzene (7.80 g, 93%).

NMR δ: 1.24(6H), 1.82(3H), 2.20(9H), 2.66(1H), 3.40(2H), 3.66(6H), 5.08(1H).

(12-b) By a procedure similar to that of Example (1-g'), the epoxy compound described above (7.8 g) was treated to give trans-1,4-dimethoxy-2,3,5-trimethyl-6-(3',7'-dimethyl-6'-hydroxy-2',7'-octadienyl)benzene (5.2 g, 65.4%).

NMR δ: 1.68(3H), 1.79(3H), 2.17(9H), 3.34(2H), 3.64(6H), 4.02(1H), 4.82(2H), 5.11(1H)

(12-c) By a procedure similar to that of Example (1-h), trans-1,4-dimethoxy-2,3,5-trimethyl-6-(3',7'-dimethyl-6'-hydroxy-2',7'-octadienyl)benzene (3.32 g, 10 m moles) was treated to give trans-1,4-dimethoxy-2,3,5-trimethyl-6-(3',7'-dimethyl-8'-chloro-2',6'-octadienyl)benzene (3.18 g, 90.8%). Colorless oil.

NMR δ: 1.66(3H), 1.76(3H), 2.16(9H), 3.36(2H), 3.84(6H), 3.92(2H), 5.10(1H), 5.52(1H).

(12-c') By a procedure similar to that of Example (1-h), trans-1,4-dimethoxy-2,3,5-trimethyl-6-(3',7'-dimethyl-6'-hydroxy-2',7'-octadienyl)benzene (3.32 g, 10 m moles) was allowed to react with thionyl bromide(2.50 g, 12 m moles) to give trans-1,4-dimethoxy-2,3,5-trimethyl-6-(3',7'-dimethyl-8'-bromo-2',6'-octadienyl)benzene (3.46 g, 87.6%). Colorless oil.

NMR δ: 1.66(3H), 1.74(3H), 2.16(9H), 3.36(2H), 3.84(6H), 3.91(2H), 5.10(1H), 6.33(1H).

(12-d) Reaction of trans-1,4-dimethoxy-2,3,5-trimethyl-6-(3',7'-dimethyl-8'-chloro-2',6'-octadienyl)benzene (175 mg, 0.5 m moles) and trans-1-(p-toluenesulfonyl)-3,7-dimethyl-2,6-octadiene(175 mg, 0.6 m mole) were carried out by the similar procedure as described in Example (1-i). The crude product was isolated and purified in the usual manner to obtain trans-1,4-dimethoxy-2,3,5-trimethyl-6-[3',7',11',15'-tetramethyl-9'-(p-toluenesulfonyl)-2',6',10',14'-hexadecatetraenyl]benzene (256 mg, 84.5%).

NMR δ: 1.24(3H), 1.62(6H), 1.68(3H), 1.79(3H), 2.17(9H), 2.40(3H), 3.24(1H), 3.34(2H), 3.66(6H), 5.10(4H, br.), 7.30(2H), 7.75(2H).

(12-e) By a procedure similar to that of Example 2-e, trans-1,4-dimethoxy-2,3,5-trimethyl-6-[3',7',11',15'-tetramethyl-9'-(p-toluenesulfonyl)-2',6',10',14'-hexadecatetraenyl]benzene (200 mg) was treated to give trans-1,4-dimethoxy-2,3,5-trimethyl-6-(3',7',11',15'-tetramethyl-2',6',10',14'-hexadecatetraenyl)benzene (120 mg, 80%).

NMR δ: 1.58(9H), 1.67(6H), 1.78(3H), 1.98 & 2.02(12H), 2.20(9H), 3.37(2H), 3.66(6H), 5.0–5.20(4H).

(12-e) In dioxane (10 ml) and ether (10 ml) was dissolved trans-1,4-dimethoxy-2,3,5-trimethyl-6-(3',7',11',15'-tetramethyl-2',6',10',14'-hexadecatetraenyl)benzene (113 mg, 0.25 m mole) and the solution was cooled to 0° C. To this was added silver (II) oxide (400 mg) and 6.4 N-nitric acid (0.4 ml) with stirring. The reaction was conducted under the same conditions for 15 minutes. Isopropyl ether and water were added to the reaction mixture and the organic layer was separated. The product was treated in the usual manner and the resulting crude product was chromatographed on silica gel (10 g). A first fraction eluted with n-hexane-isopropyl ether (2:1) was discarded and subsequent fractions were concentrated to give trans-2,3,5-trimethyl-6-(3',7',11',15'-tetramethyl-2',6',10',14'-hexadecatetraenyl)-1,4-benzoquinone (78 mg, 74%). Yellow oil.

NMR δ: 1.58(9H), 1.67(6H), 1.76(3H), 1.98 & 2.02(12H), 2.06(9H), 3.20(2H), 5.0–5.20(4H).

EXAMPLE 13

(13-a) By procedures similar to those of Examples (1-a) to (1-h), ubiquinol-1 dibenzyl ether was converted into 4'-bromo-ubiquinol-1 dibenzyl ether [$C_{28}H_{31}O_4Br$, 812 mg, 79.5%, δ: 1.78(3H), 2.06(3H), 3.30(2H), 3.92(6H), 4.93(2H), 4.95 (2H), 5.34(1H), 7.18–7.60(10H)].

(13-b) This bromo-compound (511 mg, 1 m mole) was dissolved in dimethylformamide (10 ml) and, followed by the addition of sodium p-toluenesulfinate dihydrate (250 mg), the solution was stirred at room temperature for 1 hour. The product was extracted into isopropyl ether. Recrystallization from hexane yielded 4'-(p-toluene sulfonyl)-ubiquinol-1 dibenzyl ether [$C_{35}H_{38}O_6S$, 505 mg, 86%; melting point: 105°–106° C., δ: 1.78(3H), 1.92(3H), 2.31(3H), 3.32(2H), 3.60(2H), 3.37(3H), 3.92(3H), 4.85(1H), 4.86(2H), 4.91(2H), 7.36(10H), 7.14 & 7.60(4H)].

EXAMPLE 14

(14-a) By procedures similar to those of Examples (1-a) to (1-h), ubiquinol-2 dibenzyl ether (2.0 g) was converted into 8'-chloro-ubiquinol-2 dibenzyl ether [920 mg, δ: 1.68(3H), 1.70(3H), 2.10(3H), 3.3 (2H), 3.95(3H), 3.96(3H), 4.97(4H), 5.00(1H), 5.47(1H), 7.20–7.60(10H)]. (14-b) This chloride (920 mg) was sulfonylated with sodium p-toluenesulfinate in dimethylformamide. Usual work-up gave 8'-(p-toluenesulfonyl)-ubiquinol-2 dibenzyl ether [1.05 g, δ: 1.60(3H), 1.68(3H), 2.06(3H), 2.34(3H), 3.26(2H), 3.57(2H), 3.91(6H), 4.70–5.15(2H), 4.93(4H), 7.20–7.60(10H), 7.21 & 7.64(4H)].

EXAMPLE 15

By a procedure similar to that of Example 14-b), 28'-chloroubiquinol-7 dibenzyl ether (1.51 g) was converted into 28'-(p-toluenesulfonyl)-ubiquinol-7 dibenzyl ether [1.71 g, δ: 1.60(18H), 1.68(3H), 2.02(24H), 2.12(3H), 2.42(3H), 3.30 & 3.36(2H), 3.57(2H), 3.93(6H), 4.96(4H), 5.10(7H), 7.40(10H), 7.21 & 7.64(4H)].

EXAMPLE 16

By a procedure similar to that of Example 14, menaquinol-2 dimethyl ether was converted into 8'-(p-toluenesulfonyl)-menaquinol-2 dimethyl ether [δ: 1.71 (3H), 1.77(3H), 2.35(3H), 2.38(3H), 3.53(2H), 3.63(2H), 3.88(6H), 5.90–6.20(2H), 7.26(2H), 7.40–7.51(2H), 7.67 (2H), 7.90–8.16(2H)].

EXAMPLE 17

By a procedure similar to that of Example 14, 1,3,4-trimethyl-2,5-dimethoxy-6-geranylbenzene was converted into 1,3,4-trimethyl-2,5-dimethoxy-6-[8'-(p-toluenesulfonyl)-3',7'-dimethyl-2',6'-octadienyl]-benzene (δ: 1.72(6H), 2.16(3H), 2.19(6H), 2.41(3H), 3.33(2H), 3.63(3H), 3.64 (3H), 4.97(1H), 5.02(1H), 7.27(2H), 7.64(2H)].

EXAMPLES 18–22

The coupling reaction of compound (IV) with compound (III) is carried out by the following general procedure.

In a mixture of dry tetrahydrofuran (15 ml) and dry hexamethylphosphoramide (0.5 ml) is dissolved the compound (IV)(2 m moles) and the solution is cooled to −70° C. under nitrogen. Then, n-butyllithium (in n-hexane, 15% W/W, 2 ml) is added and the mixture is stirred for 10 minutes. To the resulting carbanion is added a solution of compound (III) (2.2 m moles) in dry tetrahydrofuran (2 ml) and the mixture is stirred at the same temperature for 30 minutes. After the reaction has been completed, methanol (2 ml) is added to the reaction mixture. Then, after the temperature has been warmed to room temperature, the solvent is evaporated in vacuo. To the residue is added water (4 ml) and the product is extracted with isopropyl ether. The organic layer is washed with water, dried and concentrated under reduced pressure. The concentrate is chromatographed on silica gel (silica gel 60, Merck) using n-hexane-isopropyl ether for elution to obtain the compound (IIb). The results are summarized in Table 1.

Table 1

| Example | R¹ | Z | Y | X | n | m | No. of moles of (IV) | No. of moles of (III) | Yield of (IIb) (%) | NMR spectrum of (IIb) in CDCl₃, TMS as reference) δ |
|---------|-----|-----|-----|-----|-----|-----|-----|-----|-----|-----|
| 18 | CH₃O | Bz | Ts | Br | 1 | 9 | 2 | 2.2 | 92 | 1.50–1.68(30H), 1.79(3H), 1.98(—CH₂—), 2.30(3H), 3.32(2H)², 3.43(1H), 3.97 (6H), 4.97(4H), 5.10 (10H), 7.20–7.60(10H), 7.24 & 7.66(4H) |
| 19 | CH₃O | Bz | Ts | Cl | 2 | 2 | 2 | 2.2 | 94 | 1.50–1.65(15H), 2.09(3H), 2.38(3H), 2.70(2H), 3.42 (1H), 3.30(2H), 3.97(6H) 4.78–5.20(4H), 4.97(4H), 7.20–7.60(10H), 7.24 & 7.66(4H) |

| Example | R¹ | Z | Y | X | n | m | No. of moles of (IV) | No. of moles of (III) | Yield of (IIb) (%) | NMR spectrum of (IIb) (in CDCl₃, TMS as reference) |
|---------|-----|-----|-----|-----|-----|-----|-----|-----|-----|-----|
| | | | | | | | | | | 1.50–1.70(33H), 2.00(CH₂), |

Table 1-continued

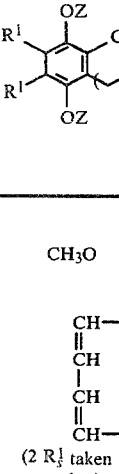

| | $R^1$ | Z | X | Y | n | m | eq | Yield (%) | NMR |
|---|---|---|---|---|---|---|---|---|---|
| 20 | CH₃O | Bz | Ts | Br | 7 | 3 | 2 | 2.2 | 87 | 2.32(3H), 3.32(2H), 3.40(1H), 3.97(6H), 4.97 (4H), 5.10(10H), 7.20–7.60 (10H), 7.24 & 7.66(4H) |
| 21 | CH=CH–CH=CH– (2 $R^1$ taken together) | CH₃ | Ts | Cl | 2 | 2 | 2 | 2.2 | 92 | 1.52(3H), 1.54(3H), 1.60 (6H), 1.73(3H), 2.33(6H) 3.40(1H), 3.50(2H), 3.84(6H) 4.6–5.2(4H), 7.42 & 7.61 (4H), 7.35–7.45(2H), 7.9–8.1(2H) |
| 22 | CH₃ | CH₃ | Ts | Cl | 2 | 2 | 2 | 2.2 | 90 | 1.56(3H), 1.59(3H), 1.63 (3H), 1.72(3H), 2.20(9H), 2.40(3H), 1.80–2.20(6H), 2.50–2.70(2H), 3.33(2H), 3.40(1H), 3.65(3H), 3.66 (3H), 4.90(1H), 4.80–5.15(3H), 7.24(2H), 7.65 (2H) |

EXAMPLE 23

(A) The compound (IIb)(1.5 m moles) is dissolved in ethylamine (20 ml) and the solution is cooled to −30° C. under argon gas. To this solution is added lithium cuttings. The addition of lithium is continued until the reaction mixture has turned blue and remains the color for 10 minutes. Following this reaction, a small amount of isoprene is added to quench the excess radical anion of lithium. The reaction mixture is concentrated under reduced pressure and the residue is acidified by the addition of cold methanol(15 ml) and phosphoric acid (3 ml). The product is extracted with isopropyl ether and isolated.

Where the resulting compound is a hydroquinone compound, it can be converted to the corresponding quinone compound by oxidation with ferric chloride as described below. Thus, the hydroquinone compound obtained by the above reaction is dissolved in 1,2-dimethoxyethane (20 ml) and a 5% aqueous solution of ferric chloride is added. The mixture is stirred at room temperature. After the reaction has been completed, the product quinone is extracted with hexane and the crude product is chromatographed on silica gel, whereupon the desired quinone compound is obtained.

The application of the above reaction procedure to the compounds (IIb) obtained in Example 18 and 20 yielded ubiquinone-10 in the yields of 73% and 76%, respectively. Similarly, ubiquinone-4 was obtained in a yield of 78% from the compound (IIb) obtained in Example 19. The ubiquinone-10 sample produced as above was in good agreement with naturally occuring ubiquinone-10 in melting point and NMR spectrum. The ubiquinone-4 was identified by comparing its IR and NMR spectra with those of a sample prepared from geranylgeraniol and 2,3-dimethoxy-5-methyl 1,4-benzoquinone.

The application of the above reductive desulfurization to the compounds obtained in Examples 21 and 22 yielded 5,8-dihydromenaquinol-4 dimethyl ether and 1,3,4-trimethyl-2,5-dimethoxy-6-geranyl-geranyl-benzene in the yields of 54% and 82%, respectively.

Treatment of the former compound with 2,3-dichloro-5,6-dicyanobenzoquinone (DDQ) yielded menaquinol-4 dimethylether.

(B-1) Oxidative demethylation of menaquinol-4 dimethylether

In a mixture of dioxane (20 ml) and ether (20 ml) is dissolved menaquinol-4 dimethylether (474 mg) and the solution is cooled to −15° C. To this solution is added silver oxide (II) (800 mg), followed by the addition of 6.4 N-nitric acid (0.8 ml) and water (0.1 ml). The reaction is conducted with stirring under the same conditions for 20 minutes. To this reaction mixture is added hexane and the organic layer is washed with water, dried and concentrated. The residue was chromatographed on silica gel using benzene for elution to obtain menaquinone-4 (257 mg, 57.9%), melting point: 35°–37° C. δ: 1.58(9H), 1.67(3H), 1.79(3H), 1.98 & 2.02(12H), 2.20(3H), 3.34 & 3.40(2H), 4.90–5.20 (4H), 7.60–7.70(2H), 8.02–8.12(2H). (B-2) Oxidative demethylation of 1,3,4-trimethyl-2,5-dimethoxy-6-geranylgeranylbenzene.

The oxidative demethylation of 1,3,4-trimethyl-2,5-dimethoxy-6-geranylgeranylbenzene was carried out by the same procedure as described in B-1) yielded the corresponding quinone compound (74%).

δ: 1.58(9H), 1.67(6H), 1.76(3H), 1.98 & 2.02(12H), 2.06(9H), 3.20(2H), 5.0–5.20(4H).

EXAMPLE 24

Synthesis of ubiquinone-7

The compound described in Reference Example 4,

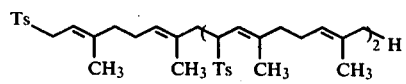

(1.75 g, 2 m moles), was dissolved in a mixture of tetrahydrofuran (30 ml) and hexamethylphosphoramide (10 ml). After the solution was cooled to −70° C. under nitrogen gas, n-butyllithium (15 W/V % solution in hexane, 6 m moles) was added. To this solution was added a tetrahydrofuran solution of 4′-bromo-ubiquinol-1 dibenzyl ether (1.1 g, 2 m moles) and the mixture was stirred under the same conditions for one hour. Thereafter, the reaction temperature was gradually warmed to −10° C. To this reaction mixture was added acetic acid (0.5 ml) and water (100 ml). The product was extracted with ethyl acetate. The organic layer was washed with water, dried and concentrated. The residue was chromatographed on silica gel using isopropyl ether-ethyl acetate (95:5) as the developing solvent mixture to obtain the coupling reaction product:

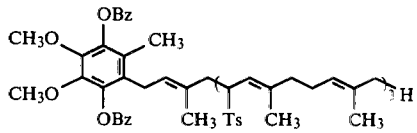

[1.86 g, 71.5% δ: 1.15(3H), 1.24(6H), 1.55(6H), 1.61(3H), 1.63(3H), 1.70(3H), 1.99(3H), 2.39(9H), 3.23(2H), 2.88 (3H), 3.95(3H), 4.9–5.3(7H), 4.89(4H), 7.2–7.60(10H), 7.24(6H), 7.64(6H)].

This compound (1.30 g, 1 m mole) was dissolved in ethylamine (20 ml) and the solution was cooled to −20° C. under argon. To this was added lithium metal (500 mg). After the solution had turned blue, it was further stirred for 10 minutes. To this blue solution was added isoprene (1 ml) to quench the excess lithium. The solvent was removed under reduced pressure and, then, tetrahydrofuran (100 ml) was added. The mixture was cooled to −10° C., followed by the addition of acetic acid (20 ml) and 30 ml of a 10% aqueous solution of ferric chloride. After the reaction, temperature was warmed to room temperature, the mixture was stirred for 3 hours. The product was extracted with isopropyl ether and chromatographed on silica gel (50 g) using hexane-isopropyl ether (1:1) for elution to obtain ubiquinone-7 (532 mg, 80%). This compound was identified by comparision of the melting point, IR and NMR spectra of this product with those of naturally occurring ubiquinone-7.

EXAMPLE 25

Synthesis of ubiquinone-10
The compound described in Reference Example 4,

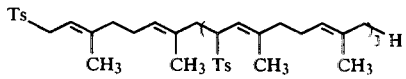

(2.32 g, 2 m moles), was dissolved in tetrahydrofuran (30 ml) and hexamethylphosphoramide (10 ml). After the solution was cooled to −70° C. under nitrogen gas, n-butyllithium (15 W/V % solution in hexane, 8 m moles) was added.

To this solution was added a tetrahydrofuran solution of 8′-chloro-unbiquinol-2 dibenzyl ether described in Reference Example 2(1.10 g). The mixture was treated as described in Example 24 to give the coupled product:

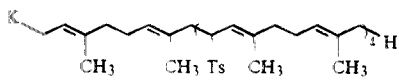

[2.61 g, 78.2%, δ: 1.22(3H), 1.24(9H), 1.52(3H), 1.55(9H), 1.61(3H), 1.64(3H), 1.68(3H), 1.3–2.1(23H), 2.43(12H), 2.9(4H), 3.32(2H), 3.8(4H), 3.97(6H), 4.9–5.4(10H), 4.97(4H), 7.2–7.6(10H), 7.26 & 7.7(16H)]. This compound (1.66 g, 1 m mole) was treated with lithium (500 mg) in ethylamine (20 ml) and the resulting hydroquinone was oxidized with ferric chloride to obtain ubiquinone-10(638 mg, 73.9%), after purification on silica gel. This product was identified with naturally occurring ubiquinone-10 by their direct comparisons of melting point, IR and NMR spectra.

EXAMPLE 26

Synthesis of menaquinone-9
The compound described in Reference Example 4,

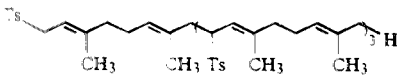

(2.32 g), was treated with n-butyllithium (15 W/V % solution in hexane, 8 m moles) by the same procedure as described in Example 24 to produce the carbanion. To the reaction mixture was added a tetrahydrofuran solution (10 ml) of 4′-chloromenaquinol dimethylether (750 mg) [δ 1.87(3H), 2.37(3H), 3.64(2H), 3.82(6H), 7.6–7.3 & 7.9–8.3(4H). Usual work-up gave the coupled compound (2.23 g, 74.2%). This product (1.50 g, 1 m mole) was subjected to desulfurization by the addition of lithium cuttings in ethylamine in the usual manner and the resulting dihydronaphthalene compound was dehydrogenated with 2,3-dichloro-5,6-dicyano-1,4-benzoquinone. The product was chromatographed on silica gel using hexane-isopropyl ether (9:1) for elution to obtain menaquinol-9 dimethyl ether [667 mg, 82%, δ: 1.59(24H), 1.67(3H), 1.78(3H), 2.0(CH$_2$), 2.35(3H), 3.37(2H), 3.68(6H), 5.10(9H), 7.2–7.6 & 7.9–8.2(4H)].

This product (600 mg) was dissolved in a solvent mixture of dioxane (20 ml) and ether (20 ml). After the solution was cooled to −15° C., silver oxide (AgO, 800 mg) was added. The mixture was stirred well and 6.4 N-nitric acid (0.8 ml) was added dropwise. The reaction was conducted under the same conditions for 10 minutes, after which the product was diluted with water (100 ml) and extracted with hexane (100 ml). Usual work-up gave menaquinone-9 (480 mg).

This product was identified by comparing with menaquinone-9 prepared from 2-methylnaphthoquinone and solanesol.

What we claim is:
1. A compound of the formula:

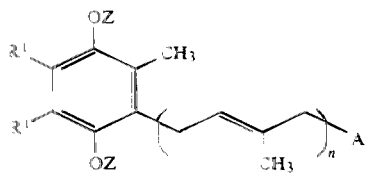

wherein R$^1$ is methoxy, Z is a protective group capable of protecting a hydroxyl group, A is halogen, arylthio, arylsulfinyl or arylsulfonyl, wherein aryl is phenyl or p-methylphenyl and n is an integer of from 1 to 9, inclusive.

2. The compound according to claim 1, wherein A is halogen.

3. The compound according to claim 1, wherein A is arylthio, arylsulfinyl or arylsulfonyl.

4. The compound according to claim 3, wherein A is arylsulfonyl.

5. The compound according to claim 4, wherein the arylsulfonyl is p-toluenesulfonyl.

6. The compound according to claim 1, wherein $R^1$ is methoxy.

7. The compound according to claim 1, wherein the protective group is methyl, methoxymethyl, ethoxymethyl or benzyl.

8. The compound according to claim 7, wherein the protective group is ethoxymethyl or benzyl.

9. The compound according to claim 1, which is 28'-chloroubiquinol-7 dibenzyl ether.

10. The compound according to claim 1, which is 28'-(p-toluenesulfonyl)-ubiquinol-7 dibenzyl ether.

11. The compound according to claim 1, which is 4'-chloroubiquinol-1 dibenzyl ether.

12. The compound according to claim 1, which is 4'-bromoubiquinol-1 dibenzyl ether.

13. The compound according to claim 1, which is 4'-bromoubiquinol-1 bis(ethoxymethyl)ether.

14. The compound according to claim 1, which is 4'-(p-toluenesulfonyl)-ubiquinol-1 dibenzyl ether.

* * * * *